US010898511B2

(12) United States Patent
Bastos et al.

(10) Patent No.: US 10,898,511 B2
(45) Date of Patent: Jan. 26, 2021

(54) MATERIALS AND METHODS RELATING TO STABILISED POLYMERIC SILICATE COMPOSITIONS

(71) Applicant: United Kingdom Research and Innovation, Swindon (GB)

(72) Inventors: Carlos André Passos Bastos, Cambridge (GB); Jonathan Joseph Powell, Cambridge (GB); Nuno Jorge Rodrigues Faria, Milton Ernest (GB); Bradley Michael Vis, Cambridge (GB)

(73) Assignee: United Kingdom Research and Innovation, Swindon (GB)

(*) Notice: Subject to any disclaimer, the term of this patent is extended or adjusted under 35 U.S.C. 154(b) by 0 days.

(21) Appl. No.: 16/169,437

(22) Filed: Oct. 24, 2018

(65) Prior Publication Data

US 2019/0224233 A1 Jul. 25, 2019

Related U.S. Application Data

(63) Continuation of application No. 15/909,095, filed on Mar. 1, 2018, now abandoned, which is a continuation of application No. 15/119,071, filed as application No. PCT/GB2015/050409 on Feb. 13, 2015, now abandoned.

(30) Foreign Application Priority Data

Feb. 14, 2014 (GB) .................................. 1402672.8

(51) Int. Cl.
| | |
|---|---|
| A61K 33/00 | (2006.01) |
| C08G 77/02 | (2006.01) |
| A61K 33/34 | (2006.01) |
| A61K 33/38 | (2006.01) |
| A61K 9/16 | (2006.01) |
| C08K 3/36 | (2006.01) |
| A61K 9/00 | (2006.01) |
| A61K 9/06 | (2006.01) |
| A61K 9/48 | (2006.01) |
| A61K 47/10 | (2017.01) |
| B82Y 30/00 | (2011.01) |

(52) U.S. Cl.
CPC ............ *A61K 33/00* (2013.01); *A61K 9/0014* (2013.01); *A61K 9/0019* (2013.01); *A61K 9/0053* (2013.01); *A61K 9/06* (2013.01); *A61K 9/16* (2013.01); *A61K 9/1611* (2013.01); *A61K 9/4866* (2013.01); *A61K 33/34* (2013.01); *A61K 33/38* (2013.01); *A61K 47/10* (2013.01); *C08G 77/02* (2013.01); *C08K 3/36* (2013.01); *B82Y 30/00* (2013.01); *C08K 2201/011* (2013.01)

(58) Field of Classification Search
CPC .................................. A61K 47/10; C08G 77/02
See application file for complete search history.

(56) References Cited

U.S. PATENT DOCUMENTS

| | | | |
|---|---|---|---|
| 1,688,228 | A | 10/1928 | Busch |
| 4,029,770 | A | 6/1977 | Willard, Sr. |
| 4,563,351 | A | 1/1986 | Caslavsky et al. |
| 5,080,900 | A | 1/1992 | Stanley |
| 5,370,876 | A | 12/1994 | Noll et al. |
| 5,534,509 | A | 7/1996 | Konishi et al. |
| 5,658,896 | A | 8/1997 | Konishi et al. |
| 5,807,951 | A | 9/1998 | Konishi et al. |
| 5,922,360 | A | 7/1999 | Bronder |
| 6,149,947 | A | 11/2000 | Hon et al. |
| 6,214,391 | B1 | 4/2001 | Ju et al. |
| 6,288,045 | B1 | 9/2001 | Kaufman |
| 6,335,457 | B1 | 1/2002 | Seguin |
| 6,692,775 | B2 | 2/2004 | Young |
| 6,884,440 | B2 | 4/2005 | Choi et al. |
| 7,014,870 | B1 | 3/2006 | Hon et al. |
| 7,915,198 | B2 | 3/2011 | Kros |
| 8,187,473 | B2 | 5/2012 | Prasad |
| 9,333,224 | B2 | 5/2016 | Stanley et al. |
| 2003/0185900 | A1 | 10/2003 | Choi et al. |
| 2004/0057958 | A1 | 3/2004 | Waggoner, Jr. et al. |
| 2004/0097467 | A1 | 5/2004 | Juturu et al. |
| 2006/0161089 | A1 | 7/2006 | Thierauf et al. |
| 2006/0178268 | A1 | 8/2006 | Kros |
| 2006/0246154 | A1 | 11/2006 | Hon et al. |

(Continued)

FOREIGN PATENT DOCUMENTS

| | | |
|---|---|---|
| CA | 2 298 762 A1 | 12/2000 |
| CN | 1 634127 A | 7/2005 |

(Continued)

OTHER PUBLICATIONS

Adenis, et al. "A dose-escalating phase I of imatinib mesylate with fixed dose of metronomic cyclophosphamide in targeted solid tumours." Br J Cancer 2013; 109:2574-8.

(Continued)

*Primary Examiner* — Kyle A Purdy
(74) *Attorney, Agent, or Firm* — McNeill Baur PLLC

(57) ABSTRACT

Stabilised and aquated polymeric silicate compositions are described in which the compositions are poorly condensed compositions in which the silicates are resorbable and are capable of undergoing efficient dissolution to provide bioavailable soluble silicic acid. In particular, stabilised and aquated polymeric silicates are described that are capable of intravenous delivery, useful in the treatment of cancer or systemic infection, or for topical administration, e.g. in the form of a solid or semi-solid ointment useful in the treatment of wounds or the prevention of bacterial infection.

35 Claims, 12 Drawing Sheets

(56) References Cited

U.S. PATENT DOCUMENTS

| | | | |
|---|---|---|---|
| 2007/0161539 | A1 | 7/2007 | Hernandez |
| 2008/0305027 | A1 | 12/2008 | Johnston et al. |
| 2009/0130230 | A1 | 5/2009 | Stanley, Sr. et al. |
| 2010/0278935 | A1 | 11/2010 | Stacey |
| 2011/0229577 | A1 | 9/2011 | Kerek |
| 2013/0130902 | A1 | 5/2013 | Roose et al. |
| 2013/0149396 | A1 | 6/2013 | Stanley et al. |

FOREIGN PATENT DOCUMENTS

| | | |
|---|---|---|
| CN | 1693195 A | 11/2005 |
| CN | 101142140 A | 3/2008 |
| RU | 2 182 006 C2 | 5/2002 |
| RU | 2 237 483 C1 | 10/2004 |
| RU | 2 280 458 C1 | 7/2006 |
| WO | WO 2006/136003 A1 | 12/2006 |
| WO | WO 2008/147468 A2 | 12/2008 |
| WO | WO 2009/018356 A1 | 2/2009 |
| WO | WO 2009/052090 A2 | 4/2009 |
| WO | 2009/127256 A1 | 10/2009 |
| WO | 2009/144087 A2 | 12/2009 |

OTHER PUBLICATIONS

Ahmad et al., "Apoptosis induction by silica nanoparticles mediated through reactive oxygen species in human liver cell line HepG2," Toxicol. Appl. Pharmacol. 259:160-168 (2012).

Akhtar et al., "Nanotoxicity of pure silica mediated through oxidant generation rather than glutathione depletion in human lung epithelial cells," Toxicology 276:95-102 (2010).

Al-Rawi et al., "Uptake and intracellular localization of submicron and nano-sized Si02 particles in HeLa cells," Arch. Toxicol 85:813-826 (2011).

Alvarez et al., "A Randomized Double Blind Study to Evaluate the Effect of an Oak Bark Extract in Two Different Topical Preparations on the Healing of Partial Thickness Wounds in Healthy Human Volunteers," 18 pages, Study at University Wound Healing Clinic (1991).

Araki et al., "Spectroscopic analysis of tissues (12). On the quantitative analysis of silicon in tumor tissue," Jpn. J. Canc. Res. 41:187-189 (1951).

Arslan C & Yalcin S. Current and future systemic treatment options in metastatic pancreatic cancer. J Gastrointest Oncol 2014; 5:280-95.

Aubert and Cannell, "Restructuring of Colloidal Silica Aggregates," Phys. Rev. Lett. 56(7):738-741 (1986).

Aveston, "Hydrolysis of Sodium Silicate: Ultracetrifugation in Chloride Solutions," J. Chem. Soc. 4444-4448 (1965).

Bagwe et al., "Surface Modification of Silica Nanoparticles to Reduce Aggregation and Nonspecific Binding," Langmuir 22:4357-4362 (2006).

Barandeh et al., "Organically Modified Silica Nanoparticles Are Biocompatible and Can Be Targeted to Neurons In Vivo," PLOS ONE 7(1):e29424 (2012).

Battye, "Upon the Medicinal Properties of Silica in Cancer, Fibroid Tumours, and Diabetes," Edinburgh Medical Journal 20:420-435 (1874).

Bauer et al., "Cytotoxicity of silica nanoparticles through exocytosis of von Willebrand factor and necrotic cell death in primary human endothelial cells," Biomaterials 32:8385-8393 (2011).

Bauer et al., "Flocculation and stabilization of colloidal silica by the adsorption of poly-diallyl-dimethyl-ammoniumchloride (PDADMAC) and of copolymers of DADMAC with N-methyl-N-vinylacetamide (NMVA)," Colloid Polym. Sci. 276:698-708 (1998).

Benezra et al., "Multimodal silica nanoparticles are effective cancer-targeted probes in a model of human melanoma," J. Clin. Invest. 121(7):2768-2780 (2011).

Bharali et al., "Organically modified silica nanoparticles:A nonviral vector for in vivo gene delivery and expression in the brain," Proc. Natl. Acad. Sci. USA 102(32):11539-11544 (2005).

Brown et al., "Influence of shape, adhesion and simulated lung mechanics on amorphous silica nanoparticle toxicity," Advanced Powder Technol. 18(1):69-79 (2007).

Burton et al., "Protection from Cancer by 'Silica' in the Water-Supply of U.S. Cities," Journal of Environmental Pathology and Toxicology 4:31-40 (1980).

Carlisle, E.M. "Silicon" in a Handbook of Nutritionally Essential Minerals, edited by B.L. O'Dell & R.A. Sunde; Marcel Dekker: New York, 1997, pp. 603-618, 18 pages.

Chang et al., "In Vitro Cytotoxicitiy of Silica Nanoparticles at High Concentrations Strongly Depends on the Metabolic Activity Type of the Cell Line,"Environ. Sci. Technol. 41:2064-2068 (2007).

Cho et al., "The impact of size on tissue distribution and elimination by single intravenous injection of silica nanoparticles," Toxicol. Lett. 189:177-183 (2009).

Choi et al., "Comparison of cytotoxic and inflammatory responses of photoluminescent silicon nanoparticles with silicon micron-sized particles in RAW 264.7 macrophages," J. Appl. Toxicol. 29:52-60 (2009).

Choi et al., "Silica-Based Nanoparticle Uptake and Cellular Response by Primary Microglia," Environ. Health Perspectives 118(5):589-595 (2010).

Christen and Fent, "Silica nanoparticles and silver-doped silica nanoparticles induce endoplasmatic reticulum stress response and alter cytochrome P4501A activity," Chemosphere 87:423-434 (2012).

Chu et al., "Cellular uptake, evolution, and excretion of silica nanoparticles in human cells," Nanoscale 3:3291-3299 (2011).

Chu et al., "Physiological pathway of human cell damage induced by genotoxic crystalline silica nanoparticles," Biomaterials 33:7540-7546 (2012).

Chung et al., "The effect of surface charge on the uptake and biological function of mesoporous silica nanoparticles in 3T3-L1 cells and human mesenchymal stem cells," Biomaterials 28:2959-2966 (2007).

Collins English Dictionary—Complete & Unabridged, 10th ed. (2015). Retrieved Jun. 24, 2015 from Dictionary.com website: http://dictionary.reference.com/browse/silicic acid, 2 pages.

Corbalan et al., "Amorphous silica nanoparticles trigger nitric oxide/peroxynitrite imbalance in human endothelial cells: inflammatory and cytotoxic effects," Int. J. Nanomed. 6:2821-2835 (2011).

Dalwadi et al., "Comparison of Diafiltration and Tangential Flow Filtration for Purification of Nanoparticle Suspensions," Pharm. Res. 22(12):2152-2162 (2005).

de Mesquita and Kerr, "Local effects of silica on tumor growth inhibition. A histological study," Arch. Geschwulstforsch. 45/7:637-647 (1975).

de Sousa Cavalcante and Monteiro, G., "Gemcitabine: Metabolism and molecular mechanisms of action, sensitivity and chemoresistance in pancreatic cancer." Eur J Pharmacol. 2014; 741C:8-16.

Deng et al., "Differential plasma protein binding to metal oxide nanoparticles," Nanotechnology20:455101, 9 pages (2009).

Deng et al., "Nanoparticle-induced unfolding of fibrinogen promotes Mac-1 receptor activation and inflammation," Nat. Nanotechnol. 6:39-44 (2011).

Denies S, Cicchelero L, Van Audenhove I & Sanders NN. Combination of interleukin-12 gene therapy, metronomic cyclophosphamide and DNA cancer vaccination directs all arms ofthe immune system towards tumor eradication. J Control Release 2014; 187:175-82.

Diaz et al., "Assessing Methods for Blood Cell Cytotoxic Responses to Inorganic Nanoparticles and Nanoparticle Aggregates," Small 4(11):2025-2034 (2008).

Downs et al., "Silica nanoparticles administered at the maximum tolerated dose induce genotoxic effects through an inflammatory reaction while gold nanoparticles do not," Mutat. Res. 745:38-50 (2012).

Drescher et al., "Toxicity of amorphous silica nanoparticles on eukaryotic cell model is determined by particle agglomeration and serum protein adsorption effects," Anal. Bioanal. Chem. 400:1367-1373 (2011).

Effati and Pourabbas, "One-potsynthesis of sub-50 nmvinyl- and acrylate-modified silica nanoparticles," Powder Technology 219:276-283 (2012).

(56) References Cited

OTHER PUBLICATIONS

Erdogdu and Hasirci, "An Overview of the Role of Mineral Solubility in Silicosis and Asbestosis," Environ. Res. Sect.A78:38-42 (1998).

Ernst et al., "Pulmonary inflammation in rats after intratracheal instillation of quartz, amorphous SiO2, carbon black, and coal dust and the influence of poly-2-vinylpyridine-N-oxide(PVNO)," Exp. Toxic Pathol. 54:109-126 (2002).

Exley, C. "Reflections upon and recent insight into the mechanism of formation of hydroxyaluminosilicates and the therapeutic potential of silicic acid."Coordination Chemistry Reviews 256: 82-88 (2012).

Fede et al., "The toxicity outcome of silica nanoparticles (Ludox®) is influenced by testing techniques and treatment modalities," Anal. Bioanal. Chem. 404:1789-1802 (2012).

Flaten and Bolviken, "Geographical Associations Between Drinking Water Chemistry and the Mortality and Morbidity of Cancer and Some Other Diseases in Norway," The Science of the Total Environment 102:75-100 (1991).

Follows, D., et al. "Beta-casein adsorption atthesilicon oxide-aqueous solution interface: calcium ion effects." Biomacromolecules (2004); 5: 319-325.

Fruijtier-Polloth, "The toxicological mode of action and the safety of synthetic amorphous silica-A nanostructured material," Toxicology 294:61-79 (2012).

Gautam et al., "Inhibition of Experimental Lung Metastasis by Aerosol Delivery of PEI-p53 Complexes," Mol. Ther. 2(4):318-323 (2000).

Gao et al., "Influence of surfactant surface coverage and aging time on physical properties of silica nanoparticles." Colloids and Surfaces A: Physicochem. Eng. Aspects (2009); 350:33-37.

Ghio et al. "Hypothesis: is lung disease after silicate inhalation caused by oxidant generation?" Lancet (1990); 336: 967-969.

Gibson et al., "Enhanced In Vivo Response to Silicate-Substituted Hydroxyapatite," Key Engineering Materials, vols. 218-220, DD. 203-206, 2002.

Gonzalez-Munoz et al., "Beer consumption reduces cerebral oxidation caused by aluminum toxicity by normalizing gene expression of tumor necrotic factor alpha and several antioxidant enzymes," Food Chem. Toxicol. 46:1111-1118 (2008).

Gualtieri et al. "Thermal decomposition of asbestos and recycling in traditional ceramics." Journal of the European Ceramic Society (2000); 20: 1409-1418.

Gulley and Martin, "Stabilization of Colloidal Silica Using Polyols," J. Colloid Interface Sci. 241:340-345 (2001).

He et al., "In Vivo Study of Biodistribution and Urinary Excretion of Surface-Modified Silica Nanoparticles," Anal. Chem. 80:9597-9603 (2008).

Health Canada, Health Products and Food Branch Inspectorate. Good Manufacturing Practices (GMP) Guidelines—2009 Edition, Version 2, 100 pages (2009).

Henrotte et al., "The regulatory role of silicon on the cell cycle," C.R. Acad. Sci. Paris 306:525-528 (1988) (with English Abstract).

Hirai et al., "Amorphous silica nanoparticles size-dependently aggravate atopic dermatitis-like skin lesions following an intradermal injection," Particle Fibre Technol. 9:3, 11 pages (2012).

Huang et al., "The effect of the shape of mesoporous silica nanoparticles on cellular uptake and cell function," Biomaterials 31:438-448 (2010).

Huang et al., "The promotion of human malignant melanoma growth by mesoporous silica nanoparticles through decreased reactive oxygen species," Biomater. 31:6142-6153 (2010).

Hwang et al., "A Physically Transient Form of Silicon Electronics," Science 337:1640-1644 (2012).

Hwang et al., "Anti-Cancer Activity of a Novel Small Molecule Compound That Simultaneously Activates p53 and Inhibits NF-kB Signaling," PLOS ONE 7(9):e44259,11 pages (2012).

Iler, "Colloidal Components in Solutions of Sodium Silicate,"ACS Symposium Series, vol. 194, Chapter 7, pp. 95-114 (1982).

Iler, R. K., The chemistry of silica: Solubility, polymerisation, colloid and surface properties, and biochemistry. John Wiley & Sons: NewYork, 1979, p. 11.

International Preliminary Report on Patentability, 8 pages, PCT appl. No. PCT/EP2009/005717 (dated Feb. 1, 2011).

Jacobs and Tomczak, "Evaluation of Bensal HP for the Treatment of Diabetic Foot Ulcers," Adv. Skin Wound Care 21:461-465 (2008).

Jacobson et al., "Short Analytical Review, Epidemiology and Estimated Population Burden of Selected Autoimmune Diseases in the United States" Clinical Immunology and Immunopathology, vol. 84, No. 3, Sep., pp. 223-243, 1997.

Jeong-Hwan et al., "Single and repeated oral dosetoxicity studies of titanium dioxide nanoparticles," Toxicol. Lett. 211S:S198, Abs. No. P33-03 (2012).

Jiang L, Yang KH, Guan QL, Mi DH & Wang J., Cisplatin plus etoposide versus other platin-based regimens for patients with extensive small-cell lung cancer: a systematic review and meta-analysis of randomised, controlled trials. Intern Med J 2012; 42:1297-309.

Jugdaohsingh et al., "Oligomeric but not monomeric silica prevents aluminum absorption in humans," Am. J. Clin. Nutr. 71:944-949 (2000).

Jugdaohsingh, R. "Silicon and bone health," The Journal of Nutrition, Health & Aging (2007); 11, 99-110.

Jugdaohsingh, et al., "Is there a Biochemical Role for Silicon?" Metal Ions in Biology and Medicine (2008); 10: 45-55, John Lobbey Eurotext: Montrouge, 13 pages.

Jung et al., "Quantitative Analysis and Efficient Surface Modification of Silica Nanoparticles,"J. Nanomater. vol. 2012, Article ID 593471, 8 pages (2012).

Kerek and Voicu, "Sub-Nano Silicic Acid, The Putative Biologically Active Form of Silica," Basic Clin. Pharmacol. Toxicol. 109(Suppl. 1):26, Abs. No. 010 (2011).

Kim et al., "Comparative study of cytotoxicity, oxidative stress and genotoxicity induced by silica nanomaterials in human neuronal cell line," Mol. Cell Toxicol. 6:6337-6344 (2010).

Kim et al., "Comparative study on transcriptional responses of human neuronal cells to silica nanoparticles with different stabilizers," BioChip J. 4(4):296-304 (2010).

Kim et al., "Gene expression profiling associated with treatment of positive charged colloidal silica nanoparticle in human neuroblastoma cells," BioChip J. 5(4):317-326 (2011).

Kim, et al., "Polymer Dynamics in PEG-Silica Nanocomposites: Effects of Polymer Molecular Weight, Temperature and Solvent Dilution." Macromolecules (2012); 45: 4225-4237.

Kreuter et al., "Apolipoprotein-mediated Transport of Nanoparticle-bound Drugs Across the Blood-Brain Barrier," J. Drug Target. 10(4):317-325 (2002).

Ku et al., "The blood-brain barrier penetration and distribution of PEGylated fluorescein-doped magnetic silica nanoparticles in rat brain," Biochem. Biophys. Res. Commun. 394:871-876 (2010).

Kumar et al., "In Vivo Biodistribution and Clearance Studies Using Multimodal Organically Modified Silica Nanoparticles," ACS Nano 4(2):699-708 (2010).

Lee et al., "The comparative effects of mesoporous silica nanoparticles and colloidal silica on inflammation and apoptosis," Biomaterials 32:9434-9443 (2011).

Li et al., "Size-dependentcy to toxicity of amorphous silica nanoparticles in human hepatoma HepG2 cells," Toxicology in Vitro 25:1343-1352 (2011).

Lin and Haynes, "Impacts of Mesoporous Silica Nanoparticle Size, Pore Ordering, and Pore Integrity on Hemolytic Activity," J. Am. Chem. Soc. 132:4834-4842 (2010).

Lin et al., "In vitro toxicity of silica nanoparticles in human lung cancer cells," Toxicol. Appl. Pharmacol. 217:252-259 (2006).

Linthicum, "Ultrastructural effects of silicic acid on primary lung fibroblasts in tissue culture," Tissue Cell 33(5):514-523 (2001).

Lison et al., "Nominal and Effective Dosimetry of Silica Nanoparticles in Cytotoxicity Assays," Toxicol. Sci. 104(1):155-162 (2008).

Liu and Sun, "Endothelial cells dysfunction induced by silica nanoparticles through oxidative stress via JNK/P53 and NF-kB pathways," Biomater. 31:8198-8209 (2010).

(56) References Cited

OTHER PUBLICATIONS

Liu et al., "Single and repeated dose toxicity of mesoporous hollow silica nanoparticles in intravenously exposed mice," Biomater. 32:1657-1668 (2011).

Lu et al., "Biocompatibility, Biodistribution, and Drug-Delivery Efficiency of Mesoporous Silica Nanoparticles for Cancer Therapy in Animals," Small 6(16)1794-1805 (2010).

Lu et al., "In vitro cytotoxicity and induction of apoptosis by silica nanoparticles in human HepG hepatoma cells," Int. J. Nanomed. 6:1889-1901 (2011).

Lundqvist et al., "Protein Adsorption onto Silica Nanoparticles: Conformational Changes Depend on the Particles' Curvature and the Protein Stability," Langmuir 20:10639-10647 (2004).

Malugin et al., "Differential toxicity of amorphous silica nanoparticles toward phagocytic and epithelial cells,"J. Nanopart. Res. 13:5381-5396 (2011).

Malvindi et al., "SiO2 nanoparticles biocompatibility and their potential for gene delivery and silencing," Nanoscale 4:486-495 (2012).

Mamaeva et al., "Mesoporous silica nanoparticles in medicine—Recent advances," Adv. Drug Deliv. Rev. pii: S0169-409X (2012).

Mansour et al., "Therapy of established B16-F10 melanoma tumors by a singlevaccination of CTL/T helper peptides in VacciMax®," J. Translational Med. 5:20, 8 pages (2007).

Martin et al., "Fast aggregation of colloidal silica," Phys. Rev. A. 41(8):4379-4391 (1990).

Martin, "Slow aggregation of colloidal silica," Phys. Rev. A 36(7):3415-3426 (1987).

Martin, K.R., "The chemistry of silica and its potential health benefits." The Journal of Nutrition, Health & Aging (2007);11 (2):94-98.

McCarthy et al., "Mechanisms of Toxicity of Amorphous Silica Nanoparticles on Human Lung Submucosal Cells in Vitro: Protective Effects of Fisetin," Chem. Res. Toxicol. 25:2227-2235 (2012).

Millipore, "Protein Concentration and Diafiltration by Tangential Flow Filtration," Technical Brief, 24 pages (2003).

Mitchell et al., "Iron(III)-doped, silica nanoshells: a biodegradable form of silica,"J. Am. Chem. Soc. 12 page accepted manuscript (2012).

Mohamed et al., "Activation of stress-related signalling pathway in human cells upon SiO2 nanoparticles exposure as an early indicator of cytotoxicity,"J. Nanobiotechnol. 9:29, 14 pages (2011).

Mosby's Medical Dictionary, 8 ed. (2009). Retrieved Jun. 23, 2015 from http://medical-dictionary.thefreedictionary.com/silicic+acid.

Mossman and Glenn, "Bioreactivity of the crystalline silica polymorphs, quartz and cristobalite, and implications for occupational exposure limits (OELs)" (Critical Reviews in Toxicology, 2013, 43 (8), 632-660).

Nabeshi et al., "Amorphous nanosilica induce endocytosis dependent ROS generation and DNA damage in human keratinocytes,"Particle Fibre Technol. 8:1,10 pages (2011).

Nabeshi et al., "Effect of amorphous silica nanoparticles on in vitro RANKL-induced osteoclast differentiation in murine macrophages," Nanoscale Res. Lett 6:464, 5 pages (2011).

Napierska et al., "Oxidative Stress Induced by Pure and Iron-Doped Amorphous Silica Nanoparticles in Subtoxic Conditions," Chem. Res. Toxicol. 25:828-837 (2012).

Napierska et al., "Size-Dependent Cytotoxicity of Monodisperse Silica Nanoparticles in Human Endothelial Cells," Small 5(7):846-853 (2009).

Napierska et al., "The nanosilica hazard: another variable entity," Particle Fibre Technol. 7:39, 32 pages (2010).

National Cancer Institute (definition: solid tumor; accessed 2011), 1 page.

Office Action for EP Application No. 08840441.3, dated Nov. 27, 2013, 5 pages.

Orr et al., "Cellular recognition and trafficking of amorphous silica nanoparticles by macrophage scavenger receptor A," Nanotoxicol. 5(3):296-311 (2011).

Park and Park, "Oxidative stress and pro-inflammatory responses induced by silica nanoparticles in vivo and in vitro," Toxicol. Lett. 184:18-25 (2009).

Park et al., "In vitro developmental toxicity test detects inhibition of stem cell differentiation by silica nanoparticles," Toxicol. Appl. Pharmacol. 240:108-116 (2009).

Park et al., "In vitro evaluation of cytotoxic and inflammatory properties of silica nanoparticles of different sizes in murine RAW264.7 macrophages," J. Nanopart. Res. 13:6775-6787 (2011).

Passagne et al., "Implication of oxidative stress in size-dependent toxicity of silica nanoparticles in kidney cells," Toxicology 299:112-124 (2012).

Patwardhan et al. ,"Chemistry of Aqueous Silica Nanoparticle Surfaces and the Mechanism of Selective Peptide Adsorption," J. Am. Chem. Soc. 134:6244-6256 (2012).

Pavelic et al. "Natural zeolite clinoptilolite: new adjuvant in anticancer therapy." J. Mol. Med. (2001); 78: 708-720.

Quignard et al., "Long-term fate of silica nanoparticles interacting with human dermal fibroblasts," Biomater. 33:4431-4442 (2012).

Rabolli et al., "The cytotoxic activity of amorphous silica nanoparticles is mainly influenced by surface area and not by aggregation," Toxicol Lett. 206:197-203 (2011).

Rancan et al., "Skin Penetration and Cellular Uptake of Amorphous Silica Nanoparticles with Variable Size, Surface Functionalization, and Colloidal Stability," ACS Nano 6(8):6829-6842 (2012).

Reffitt et al., "Orthosilicic acid stimulates collagen type 1 synthesis and osteoblastic differentiation in human osteoblast-like cells in vitro," Bone 32:127-135 (2003).

Rimstidt et al. "The kinetics of silica-water reactions." Geochimica et Cosmochimica Acta (1980); 44(11): 1683-1699 (Abstract).

Rochow, E.G. The chemistry of silicon. Pergamon Texts in Inorganic Chemistry vol. 9, Pergamon: Oxford. 1973, p. 1345-1346, 8 pages.

Rose et al., "Dietary glycine inhibits the growth of B16 melanoma tumors in mice," Carcinogenesis 20(5):793-798 (1999).

Rosen et al. "High-dose methotrexate with citrovorum factor rescue and Adriamycin in childhood osteogenic sarcoma." Cancer (1974); 33: 1151-1163.

Sandberg et al., "Comparison of non-crystalline silica nanoparticles in IL-1β release from macrophages," Particle Fibre Toxicol. 9:32,13 pages (2012).

Schaefer et al., "Fractal Geometry of Colloidal Aggregates," Phys. Rev. Lett. 52(26):2371-2374 (1984).

Schlegel, "Aus der Praxis—Fur die Praxis. Grundlegende Krebsbehandlung," Hippokrates (Helsinki) 24(10):300-304 (1953) (with English translation), 19 pages.

Schubbe et al., "Size-Dependent Localization and Quantitative Evaluation of the Intracellular Migration of Silica Nanoparticles in Caco-2 Cells," Chem. Mater. 24:914-923 (2012).

Seliger et al., "Characterization ofthe Major Histocompatibility Complex Class I Deficiencies in B16 Melanoma Cells," Cancer Res. 61:1095-1099 (2001).

Shang et al., "Unfolding of Ribonuclease A on Silica Nanoparticle Surfaces," Nano Lett. 7(7):1991-1995 (2007).

Shemetov et al., "Molecular Interaction of Proteins and Peptides with Nanoparticles," ACS Nano 6(6):4585-4602 (2012).

Simpson et al. "Therapy of spontaneous mouse cancer." Annals of Surgery (1931); 93: 169-179.

So et al., "Effect of Micro/Nano Silica Particle Feeding for Mice," J. Nanosci. Nanotechnol. 8:5367-5371 (2008).

Sohaebuddin et al., "Nanomaterial cytotoxicity is composition, size, and cell type dependent," Particle Fibre Toxicol. 7:22, 17 pages (2010).

SS 20 Powder sodium silicate MSDS (National Silicates 2008), 5 pages.

Stober and Fink, " Controlled Growth of Monodisperse Silica Spheres in the Micron Size Range," J. Colloid Interface Sci. 26:62-69 (1968).

Sun et al., "Cytotoxicity and mitochondrial damage caused by silica nanoparticles," Toxicol. In Vitro 25:1619-1629 (2011).

Svensson, 0., Kurut, A., and Skepo, M. Adsorption of β-casein to hydrophilic silica surfaces. Effect of pH and electrolyte. Food Hydrocolloids 36:332-338 (2014).

(56) References Cited

OTHER PUBLICATIONS

Tacker. (1999). Milestones in the Biochemistry of Silicon: From Basic Research to Biotechnological Applications. Angew. Chem. Int. Ed. 38:3015-3018.

Tamba et al., "New Experimental Data on the Bioavailability and Blood Brain Barrier Penetration of a Systemically Administered Silica Nanoparticles," Basic Clin. Pharmacol. Toxicol. 109(Suppl. 1):132, Abs. No. P231 (2011).

Taylor et al., "Soluble Silica with High Affinity for Aluminum under Physiological and Natural Conditions," J. Am. Chem. Soc. 119:8852-8856 (1997).

Thamatrakoln and Hildebrand, "Analysis of Thalassiosira pseudonana Silicon Transporters Indicates Distinct Regulatory Levels and Transport Activity through the Cell Cycle," Eukaryotic Cell 6(2):271-279 (2007).

Thomassen et al., "Letter to the Editor Regarding the Article by Wittmaack," Chem. Res. Toxicol. 25:4-6 (2012).

Tiberg, F., et al. "Beta-casein adsorption at the silicon oxide-aqueous solution interface." Biomacromolecules. 2: 844-50 (2001).

Trewyn et al., "Biocompatible mesoporous silica nanoparticles with different morphologies for animal cell membrane penetration," Chem. Eng. J. 137:23-29 (2008).

Uboldi et al., "Amorphous silica nanoparticles do not induce cytotoxicity, cell transformation orgenotoxicity in Balb/3T3 mouse fibroblasts," Mutation Res. 745:11-20 (2012).

Uekawa et al., "Synthesis and Characterization of Titania-Sugar Alcohol Complex Nanoparticles." J. Ceramic Soc. Jpn. 114(10):807-813 (2006).

Uppal et al., "Photodynamic Action of Rose Bengal Silica Nanoparticle Complex on Breast and Oral Cancer Cell Lines," Photochem. Photobiol. 87:1146-1151 (2011).

Vail, J. G., Soluble Silicates in Industry. American Chemical Society Monograph Series. The Chemical Catalog Company: New York, 1928, p. 443, 5 pages.

Van Den Boorn et al.,"Effective Melanoma Immunotherapy in Mice by the Skin-Depigmenting Agent Monobenzone and the Adjuvants Imiquimod and CpG," PLOS ONE 5(5):e10626, 12 pages (2010).

Vlasova et al., "The Adsorption of Biogenic Amines on the Surface of Highly Dispersed Silica from Aqueous Solutions," Colloid J. 68(3):384-386 (2006).

Wang et al., "Oxidative mechanisms contribute to nanosize silican dioxide-induced developmental neurotoxicity in PC12 cells," Toxicol in Vitro 25:1548-1556 (2011).

Wang et al., "Oxidative stress contributes to silica nanoparticle-induced cytotoxicity in human embryonic kidney cells," Toxicol. in Vitro 23:808-815 (2009).

Wang et al., "Silica Nanoparticles Suppress Fibronectin-Mediated Adhesion and Migration in Normal Human Keratinocytes," J. Nanosci. Nanotechnol. 12:293-299 (2012).

Waters et al., "Macrophage Responses to Silica Nanoparticles are Highly Conserved Across Particle Sizes," Toxicol. Sci. 107(2):553-569 (2009).

Windholz, M., The Merck Index, 10th ed., Merck & Co: New Jersey, 1983, 8326, pp. 1220 and 1221, 4 pages.

Windholz, M., The Merck Index. Merck & Co.: New Jersey, 1983, pp. 1220 and 1241, 3 pages.

Winslow, "New Cancer Drugs Use Body's Own Defenses," Wall Street Journal, 2 pages (2012).

Wittmaack, "Excessive Delivery of Nanostructured Matter to Submersed Cells Caused by Rapid Gravitational Settling," ACS Nano 5(5):3766-3778 (2011).

Wittmaack, "Novel Dose Metric for Apparent Cytotoxicity Effects Generated by in Vitro Cell Exposure to Silica Nanoparticles," Chem. Res. Toxicol. 24:150-158 (2011).

Wittmaack, "Reply to the Letter to the Editor Regarding My Article on Dose Metrics in Nanotoxicity Studies (Wittmaack, 2011)," Chem. Res. Toxicol. 25:7-10 (2012).

Wottrich et al., "Biological effects of ultrafine model particles in human macrophages and epithelial cells in mono- and co-culture," Int. J. Hyg. Environ. Health 207:353-361 (2004).

Wu et al., "Neurotoxicity of Silica Nanoparticles: Brain Localization and Dopaminergic Neurons Damage Pathways," ACS Nano 5(6):4476-4489 (2011).

Xiao et al., "Dodecagonal tiling in mesoporous silica," Nature 487:349-353 (2012).

Xie et al., "Biodistribution and toxicity of intravenously administered silica nanoparticles in mice,"Arch. Toxicol. 84:183-190 (2010).

Xu et al., "Effects of nano-sized silicon dioxide on the structures and activities of three functional proteins," J. Hazard. Mater. 180:375-383 (2010).

Xu et al., "Effects of SiO2 nanoparticles on HFL-1 activating ROS-mediated apoptosisvia p53 pathway," J. Appl. Toxicol. 32:358-364 (2012).

Yang et al., "Comparative study of cytotoxicity, oxidative stress and genotoxicity induced by four typical nanomaterials: the role of particle size, shape and composition," J. Appl. Toxicol. 29:69-78 (2009).

Ye et al., "In vitro toxicity of silica nanoparticles in myocardial cells," Environ. Toxicol. Pharmacol. 29:131-137 (2010).

Ye et al., "Nano-SiO2 induces apoptosis via activation of p53 and Bax mediated by oxidative stress in human hepatic cell line," Toxicol. in Vitro 24:751-758 (2010).

Yu et al., "Impact of Silica Nanoparticle Design on Cellular Toxicity and Hemolytic Activity,"ACS Nano 5(7):5717-5728 (2011).

Yu et al., "Influence of Geometry, Porosity, and Surface Characteristics of Silica Nanoparticles on Acute Toxicity: Their Vasculature Effect and Tolerance Threshold," ACS Nano 6(3):2289-2301 (2012).

Yu et al., "Toxicity of amorphous silica nanoparticles in mouse keratinocytes," J. Nanopart. Res. 11:15-24 (2009).

Zangi and Filella, "Transport routes of metalloids into and out of the cell: A review ofthe current knowledge," Chemico-Biol. Interact. 197:47-57 (2012).

Zhang et al., "Processing pathway dependence of amorphous silica nanoparticle toxicity-colloidal versus pyrolytic," J. Am. Chem. Soc. Accepted manuscript, 48 pages (2012).

Zhang et al., "ZnO, TiO2, SiO2, and Al2O3 Nanoparticles-induced Toxic Effects on Human Fetal Lung Fibroblasts," Biomed. Environ. Sci. 24(6):661-669 (2011).

PCT/US2008/079802, International Search Report dated Nov. 25, 2009, 7 pages.

PCT/US2008/079802, Written Opinion dated Nov. 25, 2009, 9 pages.

PCT/US2008/079802, International Preliminary Report on Patentability dated Apr. 20, 2010, 10 pages.

PCT/GB2015/050409, International Search Report and Written Opinion, dated Apr. 24, 2015, 9 pages.

PCT/GB2015/050409, International Preliminary Report on Patentability dated Aug. 16, 2016, 6 pages.

Material Safety Data Sheet, Potassium Silicate Solution, Yoneyama Pharmaceutical Co., Ltd., BD0020, revised Jun. 5, 2013, 4 pages, and its machine English translation, 5 pages.

MATERIALS AND METHODS RELATING TO STABILISED POLYMERIC SILICATE COMPOSITIONS

FIELD OF THE INVENTION

The present invention relates to materials and methods relating to stabilised polymeric silicate compositions, and in particular to processes for producing stabilised polymeric silicate compositions, to compositions obtainable using the processes and their uses, in particular in therapy.

BACKGROUND OF THE INVENTION

Silicon is an environmentally ubiquitous element and adult humans in the Western world ingest about 15 to 50 mg per day currently. Naturally it occurs as silicates wherein silicon links to oxygen atoms. Silicic acid and silica are also terms used for such structures. These range from the simplest mono silicic acid, also termed ortho, to silica particles. Its precise biological role is not yet understood but much evidence points to an important role in connective tissue health (Jugdaohsingh et al., 2008). Whilst quintessential connective tissues include bone, joints, blood vessels, skin, hair and nails, there is also notable evidence for dietary, supplemental, or therapeutic benefit of soluble or polymeric silicate in a wide array of medical conditions that include, but are not limited to, osteoporosis, osteopenia and other musculoskeletal and joint disorders, cancers of all types, various skin conditions, vascular, cardiovascular and coronary heart diseases, inflammatory diseases, autoimmune diseases, Alzheimer's disease and varying forms of cognitive impairment, infections of various types, wounds and ulcers, gastrointestinal, liver, kidney and immune related disorders and hormone related changes and disorders. Beneficial nutritional and therapeutic effects of silicate appear to extend to other animals, especially other mammals.

Silicate has been used as an oral nutritional supplement, although achieving a formulation that allows effective acquisition (absorption) following dosing is not straightforward.

Silicon in its naturally occurring inorganic form is soluble as orthosilicic acid. However, its concentration, e.g. in drinking water, needs to be relatively low (1.7 mM) as, under natural conditions, this is the maximum equilibrium solubility of aqueous silicate at pHs<9 to prevent the onset of irreversible polymerisation of particles that gradually condense and/or increase in size and then are not easily re-solubilized. This behaviour has bedevilled the development of silicate supplements as concentrated forms do not dissolve in the gut to enable absorption, whilst dilute forms result in large quantities of supplement (e.g. 20-100 ml/day) needing to be ingested.

Normally, certain chemical moieties such as ligands may be used to bind and render soluble cations/anions that otherwise would precipitate at physiological pH, but silicate is awkward because the monomer typically has greater affinity for itself (i.e. to undergo self-assembly) than for any other molecules, and the higher the concentration of silicon the more difficult it becomes to arrest its self-assembly in aqueous solution. This has led to alternate strategies for producing bioavailable and therapeutically useful silicate composition being pursued.

U.S. Pat. No. 5,807,951 (Nippon Zoki Pharmaceutical Co., Ltd) describes a process for producing silicate polymers by adding acid to a silicate solution. Optionally a saccharide or sugar alcohol may be added to the silicate compositions with the examples using lactose or mannitol. However, the process described in U.S. Pat. No. 5,807,951 requires a final drying step, between 150° C. and 250° C., to produce a dry lyophilised composition. However, as described further below, the use of heating, and any other form of drying to a powder, has the significant disadvantage of causing the formation of condensed silicates with corresponding poor resorbability.

US 2011/0229577 (Kerek) discloses silicic acid particles having shell-like structures in which the particles condense under conditions in which the pH of the reaction mixture is first reduced and then increased, leading to a composition said to be at a pH 2.1 or a pH greater than 9.2.

Kim et al. (Macromolecules, 45: 4225-4237, 2012) describes the production of nanocomposite melts formed from a mixture of silicate nanoparticles and ethanol mixed with a defined mass of PEG. The samples were heated in a vacuum oven to remove residual ethanol. The vacuum oven was then purged several times with nitrogen followed by evacuation of the chamber to remove oxygen, yielding the polymer nanocomposites. Importantly, the silicate nanoparticles were relatively large (44±5 nm). Also, these were synthesized based on a base-catalysed hydrolysis and condensation of tetraethylorthosilicate (TEOS) which yields condensed silicates.

Gao et al (Colloids and Surfaces A: Physicochem. Eng. Aspects 350: 33-37, 2009) precipitated silicates in the presence of PEG but the process employed required first calcination at 550° C., producing highly condensed materials that are distinct from those described herein.

Given the disadvantages of the prior art silicate composition formulations, the conditions used to formulate them and the manner in which they need to be administered, it remains an unsolved problem in the art to improve the properties of stabilised polymeric silicate acid compositions. It would be advantageous to provide compositions in which the silicates are resorbable, i.e. are capable of undergoing efficient dissolution to provide bioavailable soluble silicic acid, and in which the compositions do not tend to form condensed forms of silicates, as occurs in the prior art when compositions are dried.

Alternatively or additionally, it would further be advantageous if the other components of the stabilised polymeric silicate compositions were suitable for administration to a human or animal subject, e.g. without the dilution or other steps needed with prior art silicate supplements. Alternatively or additionally, it would be advantageous if the compositions were capable of providing amounts of stabilised polymeric silicates suitable for use in therapy, as compared to prior art compositions that contain only low levels of bioavailable silicate present as appropriately resorbable polymeric silicates.

SUMMARY OF THE INVENTION

Broadly, the present invention addresses the need in the art to provide stabilised and aquated polymeric silicates, to compositions obtainable using the processes and their uses, that are suitable for administration as therapeutic agents and supplements. In particular, the present invention addresses the provision of stabilised and aquated polymeric silicates that are capable of intravenous delivery or for topical administration, e.g. in the form of a solid or semi-solid ointment. These formulations may be useful in the treatment of wounds.

As well known in the art, there is an equilibrium between soluble silicic acids and increasingly condensed silicate compositions. Accordingly, in the present invention, "stabilised polymeric silicate composition" includes polymeric silicic acid and nanosilicate particles having the properties described herein, as well as soluble forms of silicic acid and polysilicic acid that they are in equilibrium with in the composition or in a formulation comprising it.

Evidence is emerging in the art that suggests that silicic acid is beneficial for health and disease prevention or cure in humans and other animals. In general, the compositions of the present invention comprise polymeric silicate compositions in which the natural tendency of polymeric silicates to grow to form higher order polysilicates and silicate particles is inhibited by the inclusion of substances such as organic compounds that are capable of acting as growth retardants, i.e. which inhibit the natural tendency of polysilicic acid to grow to form gels and more condensed silicate particles or polymers and particles larger than those of the desired size. Moreover, in some aspects, the present inventors have found that this approach means that the compositions are stable at physiological acceptable pHs, especially neutral or mildly acidic pH or mildly alkaline pH.

A further advantage of the method described herein is that through the selective control of pH, silicon concentration, and stabiliser concentration during the synthesis, the particle size may be tailored from small polymers of less than 1 nm diameter up to 20 nm diameter depending upon the desirable particle size and that this may then be stabilised according to the invention outlined to enable administration to a subject or animal at the chosen particles size. It will be clear to those skilled in the art that a particle size refers to a range of sizes and the number quoted herein refers to the average diameter, most commonly mean diameter of that range of particles.

The inventors have discovered that polyalkylene glycols such as PEG and/or sugars such as sucrose are advantageous size stabilisers and/or stability modulators of poorly condensed nanosilicates that may then find use for oral, parenteral or topical administration. Sucrose is especially advantageous for oral or parenteral administration as it is a well known, extremely safe molecule with a long history of use in intravenous iron products, for example. In contrast, PEG is especially well suited for topical delivery of silica as it forms a cream or an ointment and is available in a range of different molecular weights, allowing the tailoring of viscosity and other physical parameters that may be desirable in the final ointment. The application of the present invention to topical products has therapeutic use for wound healing and as in anti-infective compositions.

Accordingly, in a first aspect, the present invention provides a process for producing a stabilised polymeric silicate composition comprising polymeric silicic acid and nanosilicate particles having mean diameters of 20 nm or less, the process comprising the steps of:

(a) providing an aqueous solution of a soluble silicate at a pH greater than or equal to 9.5;

(b) reducing the pH of the silicate solution to cause polymerisation of the silicate to form polymeric silicic acid and nanosilicate particles; and (c) simultaneously or sequentially with steps (a) and/or (b) adding to the silicate solution a stabilising agent that comprises a polyalkylene glycol and/or a sugar thereby producing a stabilised silicate composition in which the stabilising agent inhibits formation of condensed silicates;

wherein the stabilised polymeric silicate composition is aquated and wherein the process does not involve drying the composition or heating it above 100° C.

In a further aspect, the present invention provides a stabilised polymeric silicate composition comprising polymeric silicic acid and nanosilicate particles having mean diameters of 20 nm or less as obtainable by the process of any one of the preceding claims.

Silicate nanoparticles that are transiently stable in vivo may have suitable roles for re-activation of the immune system to help treat infections and cancers, for example. Cancers include melanoma, skin cancers, lung cancer, pancreatic cancer, colon rectal and other splanchnic cancers, gastric cancer, breast cancer, lymphomas, leukaemias, uterine cancers, prostate cancer, oesophageal cancer, bone cancers, bladder cancers, cervical cancer, endometrial cancer, brain cancer, eye cancers, ovarian cancer, testicular cancer, liver cancer, renal cancer, head and neck cancers and includes metastatic and primary cancers. Infection includes, but is not limited to: infection with viruses, retroviruses and bacteria such as mycobacteria, Gram positive bacteria and Gram negative bacteria, as well as helminths, parasites and other infectious agents.

The transiently stable silicate nanoparticles may also act as a reservoir for the release of silicic acid that itself is effective in enhancing connective tissue health and may be useful in osteoporosis, fracture healing, joint diseases, skin diseases, blood vessel disorders, or for nutritional supplementation to ensure adequate supply of silicate.

As such, administration may be by topical application, oral administration or parenteral administration, the latter especially by intravenous administration.

In a further aspect, the present invention provides a stabilised polymeric silicate composition comprising polymeric silicic acid and nanosilicate particles having mean diameters of 20 nm or less as defined herein for use in a method of treatment.

In a further aspect, the present invention provides a stabilised polymeric silicate composition comprising polymeric silicic acid and nanosilicate particles having mean diameters of 20 nm or less as defined herein for use in a method of promoting wound healing and/or treating or preventing bacterial infection, wherein the composition is formulated for topical administration.

In a further aspect, the present invention provides a silicate-containing supplement comprising a stabilised polymeric silicate composition comprising polymeric silicic acid and nanosilicate particles having mean diameters of 20 nm or less as defined herein for use in the delivery of silicic acid to a human or animal subject. The composition may be employed in the treatment of conditions ameliorated by administration of silicates.

In a further aspect, the present invention provides the use of a stabilised polymeric silicate composition comprising polymeric silicic acid and nanosilicate particles having mean diameters of 20 nm or less as defined herein in the manufacture of a medicament for the treatment of a condition ameliorated by administration of silicate.

In a further aspect, the present invention provides the use of a stabilised polymeric silicate composition comprising polymeric silicic acid and nanosilicate particles having mean diameters of 20 nm or less as defined herein as a silicate containing supplement.

In a further aspect, the present invention provides a composition comprising a stabilised polymeric silicate composition comprising polymeric silicic acid and nanosilicate particles having mean diameters of 20 nm or less as defined herein for use in therapy.

In a further aspect, the present invention provides a method of treating a condition ameliorated by administration of silicic acid, the method comprising administering to a subject in need of treatment, a therapeutically effective amount of a composition comprising a stabilised polymeric silicate composition comprising polymeric silicic acid and nanosilicate particles having mean diameters of 20 nm or less as defined herein.

In a further aspect, the present invention provides a silicate-containing supplement comprising a stabilised polymeric silicate composition comprising polymeric silicic acid and nanosilicate particles having mean diameters of 20 nm or less as obtainable by the process of as described herein for use in the delivery of transiently stable silicate polymers to a human or animal subject.

In a further aspect, the present invention provides a stabilised polymeric silicate composition for use in a method of treatment, wherein the composition comprising polymeric silicic acid and nanosilicate particles having mean diameters of 20 nm or less and a stabilising agent comprising sucrose and/or a polyalkylene glycol, wherein composition is formulated for intravenous (IV) administration via an intravenous drip.

In a further aspect, the present invention provides a stabilised polymeric silicate composition for use in a method of treatment, wherein the composition comprising polymeric silicic acid and nanosilicate particles having mean diameters of 20 nm or less and a stabilising agent comprising a polyalkylene glycol, wherein composition is formulated for topical administration, the composition is for use in a method of promoting wound healing and/or treating or preventing bacterial infection.

Embodiments of the present invention will now be described by way of example and not limitation with reference to the accompanying figures. However, various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

BRIEF DESCRIPTION OF THE FIGURES

FIG. 2A shows lack of stability of materials after synthesis (70 mM; pH8) and FIG. 2B shows lack of stability in simulated physiological conditions (40 mM, pH 7.0). The materials reported in these figures were synthesized according to U.S. Pat. No. 5,807,951 for comparison with the stabilised polymeric silicate compositions of the present invention.

FIG. 5A) Dissolution rates for small amorphous nano-silicates (SANS) and commercial condensed silicates (Ludox SM30®) in water (pH 7.2±0.3). FIG. 5B) Dissolution rates of small amorphous nano-silicates (SANS), autoclaved SANS, and PEG-stabilised ultra small amorphous nano-silicates (uSANS) as well as and non-stabilised uSANS.

DETAILED DESCRIPTION

The biological role of silicon and the chemistry of silicates

Figure 1:
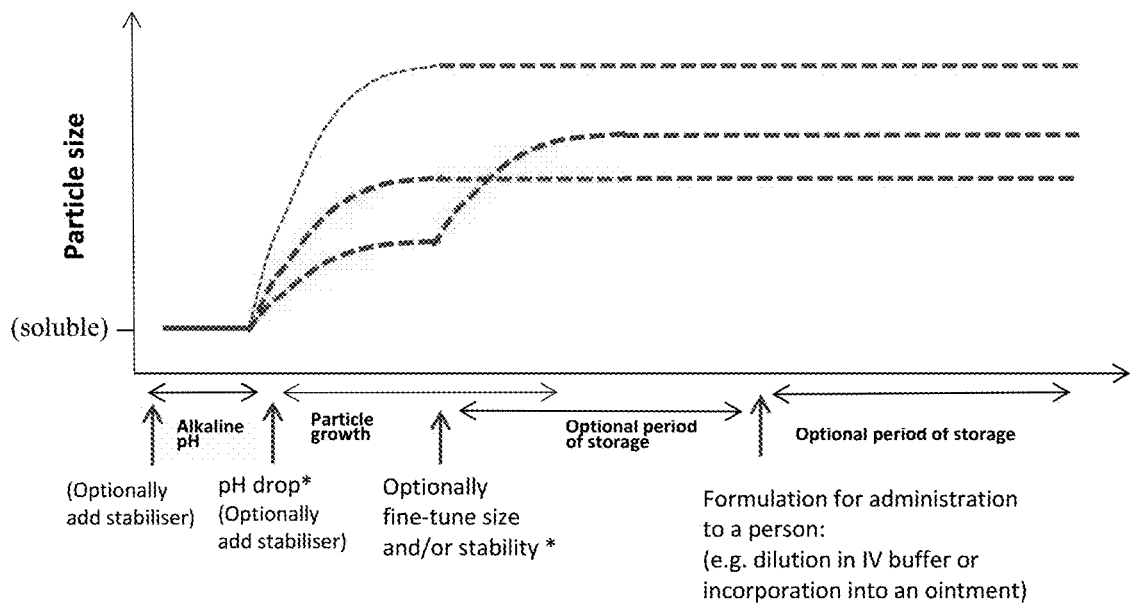
FIG. 1. Schematic representation of particle size at various stages of three theoretical synthesis processes shown by the dashed line.

Evidence suggests that silicic acids whether monomeric or polymeric are beneficial for health and disease prevention or cure in humans and other animals. However, as described above, the fundamental problem in the art is that silicic acid, the monomer of which is represented as $Si(OH)_4$, self assembles and at pHs≤9.0 and concentrations above the maximum solubility of aqueous silicate (1.7 mM at 25° C., see FIG. 1 of Jugdaosingh et al., supra) it forms insoluble species. As is well known in the art, there is an equilibrium between soluble silicic acids and increasingly condensed silicate species, namely mono-, di- and tri-silicic acids, polysilicic acids and silicate particles. The process of growth from solutions of silicic acid involves evolution where the single unit grows in size and becomes more and more evolved (i.e. less labile, soluble and/or dissolvable) and, thus, less able to return towards $Si(OH)_4$ in the absence of added alkali. Growth can include polymerisation, agglomeration, aggregation or an increase in size due to surface deposition of soluble species. The growth of polysilicic acids eventually leads to gel formation under suitable conditions. These factors make it extremely difficult to stabilise silicate compositions above these concentrations of aqueous silicate and at physiologically relevant pH.

The dosing of silicate is therefore a challenge because the dosage must deliver silicon as required for a desirable effect in terms of both concentration and chemical form, and at a pH that is compatible with physiological health and in a manner that will avoid persistent nanoparticles of silicate that may have adverse effects to health. Of particular note is that during application of a dosage, three notable changes generally occur due to the physiological environment. Firstly, there will be dilution by the physiological fluids, and secondly there will be a pH change, and thirdly there will be a change in the ionic strength. The net effect of these influences will determine the behaviour of the dosed silicate. In these respects, the present inventors have found that certain conditions can be achieved to generate metastable silicate dosages, at compatible pHs for application to humans or animals and that upon a change in the chemical environment, as may be brought about by a physiologically relevant system, desirable properties of the silicate dosage are achieved, or retained.

Stabilised Polymeric Silicate Compositions

The present invention provides processes for producing a stabilised polymeric silicate composition comprising polymeric silicic acid and nanosilicate particles, in particular particles having mean diameters of 20 nm or less. In the processes of the present invention, polymerisation of silicates and particle size growth is controlled and the resulting particles are rendered size stable through the combination of silicate concentration, pH and/or stabiliser. This is shown schematically in FIG. 1. In some embodiments, the compositions may additionally be doped with metal cations as the present inventors have found that these may induce particle size growth and may provide the compositions with useful additional properties. Doping with copper ($Cu^+$) or silver ($Ag^+$) is preferred as this may provide the formulations with antimicrobial properties.

The stabilised and aquated polymeric silicate compositions may subsequently be formulated according to the application to which the composition is intended. If intended for topical uses, the compositions may be incorporated into an ointment (e.g. a PEG cream), which itself may confer extra stability. For intravenous applications it may be advantageous to adjust the pH and concentration of the stabilised suspension prior to administration, e.g. by dilution in an i.v. buffer. In this case, rather than long-term stability, the main goal may be size stability under physiological conditions during the therapeutic window during which the composition is administered to a subject. In some circumstances, dilution may be used to offset some of the loss in stability that the change in pH causes as silicic acid compositions are more stable at low concentrations of silicon. Accordingly, the stabilisation may provide sufficient time for the material to be used by dilution at a point of use.

One preferred feature of the present invention is that stabilisation and size control are achieved without the use of high temperatures at any stage in the process. This may be contrasted with the approach taken in U.S. Pat. No. 5,807,951 in which drying the silicates at 200° C. causes the formation of condensed forms of silicates that are then less bioavailable. Preferably, this means that the processes of the present invention are carried out at less than 100° C. and more preferably less than 70° C. Alternatively or additionally, it is preferred that stabilisation is achieved without the removal of solvent (i.e. drying), since this also favours the formation of condensed forms of silicate. There are processes known in the art to produce stable colloidal silicates but these use a combination of heat-induced ageing, and/or organic solvents, and/or drying processes at temperatures exceeding 100° C., or even 200° C. However, these strategies produce nanoparticles that are relatively large (typically larger than 20 nm) and, importantly, exhibit a high level of condensation. Overall, such high levels of condensation result in more persistent particles, as compared to the poorly condensed forms of stabilised polymeric silicates compositions of the present invention, with the potential for long-term toxicity.

Preferably, the polymeric silicates compositions of the present invention have the property of being resorbable, that is that they are poorly condensed amorphous silicates that are capable of undergoing dissolution, within therapeutically useful timescales, upon administration. The amorphous nature of polymeric silicate acid compositions and different levels of condensation and the corresponding structural arrangement of the solid phase that can be exhibited by amorphous mineral phases, may be indistinguishable by XRD analysis (or equivalent). Accordingly, in the present invention, the level of condensation can be determined by appropriate in vitro dissolution assays, whereby poorly condensed amorphous nanosilicates exhibit faster dissolution rates as compared to condensed amorphous silicates of equivalent particle size.

In one example a dissolution assay may involve taking a sample of a polymeric silicate composition and diluting it in buffer. A molybdic acid assay may be used to determine the concentration of soluble silicate present in an aliquot of the buffer over time course of the assay. As shown in the examples, the composition may be diluted in 10 mM HEPES buffer and adjusted to pH 6.7-7.0. An exemplary molybdic acid assay employs 100 μL of the test solution or standard (prepared from Sigma Aldrich Si ICP standard, 1000 mg/L)

and 200 μL molybdic acid colouring solution (0.6105 g $NH_4Mo_7$ $4H_2O$, 15 mL 0.5 N $H_2SO_4$, 85 mL $H_2O$). The assay solution is transferred to a well plate and mixed for 10 minutes. After the incubation, the absorbance (405 nm) can be measured and the concentration of soluble silicic acid determined using a standard curve. By way of example, a "poorly condensed" polymeric silicate composition will be resorbable, for example as determined in an in vitro dissolution assay in which at least 25% of the composition, and more preferably at least 35% of the composition, more preferably at least 50% of the composition, and more preferably at least 75% of the composition dissolves in 24 hours in HEPES buffer.

The polymeric silicic acid compositions of the present invention comprise soluble polysilicic acid and nanoparticles of polymeric silicic acid having mean diameters of 20 nm or less, and in some cases mean diameters that are more preferably less than 10 nm, more preferably less than 5 nm, 4 nm, 3 nm, 2 nm or 1 nm. In some embodiments, the particles may range from about 1 nm to about 2 nm, or from about 1 nm to about 3 nm, or from about 1 nm to about 4 nm, or from about 1 nm to about 5 nm, or from about 1 nm to about 10 nm, or from about 1 nm to about 15 nm, or from about 1 nm to about 20 nm, or from about 5 nm to about 20 nm, or from about 5 nm to about 15 nm, or from about 5 nm to about 10 nm, or from about 10 nm to about 15 nm, or from about 10 nm to about 20 nm, or from about 15 nm to about 20 nm.

The non-soluble nature of the polymeric silicic acid and/or nanosilicate particles may be confirmed indirectly by the molybdic acid assay mentioned above as this determines the soluble silicic acid fraction. In general, the materials will be in equilibrium with the soluble silicic acid, with typical soluble silicic acid concentration being about <2 mM at pH<9.0. The polymeric silicate compositions of the present invention may be contrasted with more condensed forms of silicates, including larger nanoparticles (e.g. preferably having an average size greater than 50 nm, and more preferably greater than 20 nm), polysilicic acid gels and silicon dioxide ($SiO_2$) the fully condensed form of silicic acid, in which —OH groups are virtually absent. The size of the particles of polysilicic acids can be determined using dynamic light scattering and it is preferred that the measurements are made on freshly prepared samples, if not stabilised. As will be understood by those skilled in the art, the polysilicic acids will be in equilibrium with other silicate species. For example, and depending on the precise conditions present, this may include smaller amounts of soluble silicic acid.

The polymeric silicic acid compositions of the present invention are aquated, that is water is present throughout their synthesis and, at least to some degree (e.g. at least 5 wt %, more preferably at least 10 wt %, at least 20 wt % water), preferably also in the final formulation, i.e. the materials are not dried or significantly heated prior to formulation and subsequent administration. It will be clear, however, that stabilisers or other formulation agents may be used at such a high concentrations that displaces water molecules from the silicate particles. As such, the water may be displaced although the formulation is not dried.

The stabilisation of the polymeric silicic acid compositions of the present invention preferably extends from their synthesis to their storage, formulation and/or administration (e.g. unwanted lack of agglomeration).

The polymeric silicate compositions of the present invention are metastable, that is the compositions possess a stability that is fit for the purpose of shelf-life of their intended use, and do not grow to any significant extent. By way of illustration, it is preferred that the polymeric silicate compositions of the present invention are storage stable, for example being stable for 3 months or more, more preferably for 6 months or more, more preferably for 12 months or more, and more preferably 24 months or more. Thus, the polymeric silicate compositions of the present invention may be produced by partial condensation of silicic acid (or silicate) molecules. These materials are metastable as discrete, non-aggregated clusters or colloids.

In the present invention, the polymeric silicate compositions include a stabilising agent, preferably a sugar and/or a polyalkylene glycol. The sugars include oligosaccharides composed of eight monosaccharides or fewer, such as monomeric, dimeric or trimeric saccharides. A preferred sugar is sucrose. The maximum number of monomeric units in the sugar is chosen such that its administration does not elicit an immune response in the subject on administration. Polyalkylene glycols are a family of polyether compounds that include polyethylene glycol (PEG) and polypropylene glycol. Examples of stabilising agents that are sugars (saccharides) include monomeric, dimeric, trimeric and polymeric sugars (saccharide), or the corresponding sugar alcohols, such as glucose, fructose, mannose, sucrose, threitol, erythritol, sorbitol, mannitol, galactitol or adonitol. In some embodiments in which the stabilising agent is a sugar, it is an oligosaccharide other than lactose. In some embodiments in which a sugar alcohol is used, it is other than mannitol. The use of sugars as stabilising agents for compositions that are administered internally is preferred in the present invention as they are safe for administration to human and animal subjects.

In some embodiments, it is possible to employ combinations of more than one different sugar(s) or polyalkylene glycol(s), e.g. two, three, four or five or more sugars or polyalkylene glycols, e.g. by adding them in step (a) and/or (b). Sugar and/or polyalkylene glycol stabilising agents are generally added at a concentration between 0.01 M and 3.0 M, and more preferably between 0.03 and 2.0 M, and most preferably between 0.1 M and 1.5 M. The skilled person can carry out routine tests to determine which combinations of sugars and/or polyalkylene glycols work best in any given situation.

The stabilised polymeric silicate compositions of the present invention may be distinguished from the compositions disclosed in US Patent Publication No: 2003/0206967 (Choi et al.) which describe a composition that comprises sodium metasilicate, borax, sodium thiosulfate, potassium carbonate and refined sugar in water. This results in a very alkaline composition having a pH of about pH 13, in contrast to pHs of the stabilised polymeric silicate compositions of the present invention, which are preferably between pH 3.0 and 9.0, more preferably between 3.0 and 8.0 and more preferably between 5.5 and 7.5. The process used to make the compositions of Choi et al. differs from the present invention as the present invention produces the compositions by lowering the pH to produce stable silicate polymers. In view of the above, it is preferred that the stabilised polymeric silicate compositions of the present invention do not comprise one or more of sodium metasilicate, borax, sodium thiosulfate, potassium carbonate, and preferably do not include borax.

In other aspects, the present invention may use carboxylic acids as stabilizing agents and the carboxylic acid may be a $C_{2-10}$ carboxylic acid, for example a dicarboxylic acid such as oxalic acid, malonic acid, glutaric acid, tartaric acid, succinic acid, adipic acid or pimelic acid, or ionised forms thereof (i.e., the corresponding carboxylate), such as adipate. Or for example a monocarboxylic acid, such as gluconic acid. Further examples of stabilizing agents are dicarboxylic acids, which may be represented by the formula HOOC—$R_1$—COOH (or an ionised form thereof), where $R_1$ is an optionally substituted $C_{1-10}$ alkyl, $C_{1-10}$ alkenyl or $C_{1-10}$alkynyl group. In general, the use of carboxylic acids in which $R_1$ is a $C_{1-10}$ alkyl group, and more preferably is a $C_{2-6}$ alkyl group, is preferred.

In some embodiments, the polymeric silicic acid compositions may be contacted with metal cations, such as $Ca^{2+}$, $Mg^{2+}$, $Ag^+$, $Al^{3+}$, $Cu^{2+}$, $Fe^{3+}$ and/or $Zn^{2+}$ as the inventors have found that this helps to stabilise the compositions against dissolution, which may be advantageous in some applications, or confer additional functional benefits (e.g. antimicrobial action, for example by including $Ag^+$ and/or $Cu^{2+}$). Without wishing to be bound by any particular theory, the present inventors believe that the cations coat the nanosilicate particles via interaction with free silanol groups (—OH) present in the materials. By way of guidance, it is preferred that the metal cation is added to provide a final concentration between 0.01 M and 1.0 M and more preferably the metal cation is added to provide a final concentration between 0.05 M and 0.5 M. Preferably, the metal cation is added to provide a Si to metal ratio of between 100:1 and 10:1, and optionally to provide a Si to metal ratio of 20:1.

The present inventors also surprisingly found that polymeric silicate acid compositions of the present invention may be further stabilised by adding a non-aqueous solvent, such as an alcohol. A preferred example of an alcohol is ethanol. By way of illustration, the non-aqueous solvent may be added between 10 and 50% v/v, or between 20 and 50% v/v or between 10 and 20% v/v. Furthermore, in some cases the present inventors found that the combination of sucrose with alcohol was particularly effective for stabilising the compositions.

In the following discussion of the steps of the processes of the present invention, it will be apparent to those skilled in the art that it may be possible to reorder some of the steps of the above process and/or for some of the steps to take place simultaneously. Others of the steps are optional as indicated above and explained further below.

In the work leading to the present invention, the inventors found that a number of factors contribute to the stability of the polymeric silicate compositions including the rate at which the pH of the starting alkaline silicate solution is lowered, the inclusion of stabilisers, notably sugars or polyalkylene glycols, the addition of metal cations and/or the addition of a non-aqueous solvent. Accordingly, the processes of the present invention may employ these approaches, alone or in any combination, to produce polymeric silicate compositions having sufficient stability for use, e.g. as supplements or therapeutic agents. The metal cations may also serve to provide antibacterial properties to the compositions (e.g. by adding $Ag^+$ or $Cu^{2+}$) and/or to inhibit dissolution of the composition as demonstrated in FIG. 20.

In some cases, in particular for the production of ultra small particles of nanosilicates ("uSANS"), the rate at which the pH of the alkaline silicate solution is lowered may have a significant effect on the stability of the resulting polymeric silicate compositions. Preferably, the pH is lowered (e.g. to a pH of less than or equal to pH 4.0 or 3.0) over a period of less than 60 seconds, more preferably less than 30 seconds, more preferably less that 10 seconds, or most preferably less that 5 seconds.

In step (a), it is preferred that the concentration of the alkaline silicate solution is between 0.05 M and 1.5 M, and more preferably is between 0.03 and 2.0 M, and most preferably between 0.1 M and 1.0 M. The use of pHs that are higher than 9.5 is also preferred in order to maintain the solubility of the silicates, and preferably in step (a) the pH of the alkaline silicate solution is about pH 10.5 or above, and still more preferably is about pH 11.5 or above. In the final polymeric silicate compositions, the concentration of silicon may be 2.5 mM or more, 5.0 mM or more, 25 mM or more, 30 mM or more, 40 mM or more, 50 mM or more, 100 mM or more, 250 mM or more, 500 mM or more. In the final stabilised polymeric silicate compositions, the concentration of silicon may be 1.5M or less, 1.0M or less, 500 mM or less, and ranges between these lower and upper limits.

In some embodiments, the reduced pH in step (b) has an effect on the type of stabilised silicate nanoparticles that can be produced. As shown in the examples, uSANS or very small particles that have mean diameters of 5 nm or less can be formed by rapidly dropping the pH from pH greater than 10 to 3.0 or less and enable concentrations of silicon up to 1 M to be used. Alternatively, SANS or small nanoparticles have mean diameters of 10 nm of less and may be formed by reducing the pH to about 7.4. In this case, lower concentrations of about 50 mM or less can be used. Accordingly, the reduced pH may be 7.4 or lower, or pH 3.0 or lower. This enables the preparation of uSANS at a low pH, as described, the pH raised to grow uSANS to SANS of a determined particle size, and the size stabilised by dropping the pH again, should this be required. Stabiliser is required at some stage in this process. These processes are an important part of the art.

In some case, the pH may be lowered and/or the suspension diluted for long term storage of stabilised aqueous suspensions. Alternatively or additionally, upon long term storage at a non-physiological pH and prior to administration to a subject, the nanosilicate suspension may be adjusted to a physiological pH, and/or diluted and/or stabiliser added.

In situations in which the silicate compositions are formulated in an ointment or cream, or where the suspension is diluted so that it has a silicon concentration of 100 mM or less, it may be preferred that the pH of the composition or a formulation containing it is raised to a physiological pH, preferably to a pH between 3.0 and 8.0, and more preferably to a pH of between 5.5 and 7.5. Conveniently, this may be done by adding a base, such as sodium hydroxide or sodium carbonate. Generally the pH of the composition should be suitable for administration, i.e. close to physiological, for example pH 7.4±1.5. The aim of this is so that administration to a subject will not result in unintended clinical outcomes, such as pain or inflammation. However, depending on the route of administration, it may be acceptable if the final formulation containing the stabilised polymeric silicate compositions has a pH in the range between pH 3 and pH 9.

The composition should be suitably stabilised, such that the particle size of the nanosilicates will remain sufficiently stable (<20 nm) for the intended application. For example, in the case of a formulation for intravenous administration, the particle size of the first storage solution (e.g. at pH<3 and 100 mM Si) will be stable for the duration of the storage period and then once diluted with a buffered i.v. solution it will remain stable first for the few hours before application and then, once administered, it will not undergo agglomeration. PEG stabilisation in topical applications would also mean that particle size would be sufficiently constant in the ointment during storage and upon application.

Formulation and Uses of Compositions

The stabilised polymeric silicate compositions of the present invention may be formulated for use in a range of biologically relevant applications, including formulation for use as pharmaceutical or nutritional compositions, and in particular as a silicate-containing supplement or therapeutic agents. The compositions of the present invention may comprise, in addition to one or more of the solid phase materials of the invention, a pharmaceutically acceptable excipient, carrier, buffer, stabiliser or other materials well known to those skilled in the art. Such materials should be non-toxic and should not interfere with the efficacy of the stabilised polymeric silicate compositions depending on their intended use. As well as having applications for the treatment or prevention of conditions in human subjects, the present invention has application in the veterinary field.

The present invention provides compositions suitable for a range of different applications in which silicic acid is provided to a subject.

In one application, the stabilised polymeric silicate compositions may be for use in oral delivery of silicic acid to a subject via the gastrointestinal tract, in particular wherein the stabiliser is a sugar. In this aspect of the invention, preferably the composition generally is for direct administration to a subject, i.e. there is no requirement for a dilution step to be carried out by the subject prior to administration. Preferably, the stabiliser is chosen from among the saccharides set out herein. Typically, the sugar will be employed in an amount between 0.01 M and 3.0 M, and more preferably between 0.03 and 3.0 M, even more preferably between 0.1 and 3.0 M, and most preferably between 0.01 M and 1.5 M. More preferably, the compositions have a pH between 1.0 and 6.0, 1.5 to 5.0, or 2.2 to 4.0, or 2.4 to 4.0. In other embodiments, the compositions have a pH between 1.5, or 2.0, or 2.5 and a pH of 6.0, or 5.5, or 5.0, or 4.5, or 4.0, or 3.5. The concentration of silicon is between 0.1M and 1.5M. These compositions may be used for silicon supplementation or for delivery of therapeutic silicate, i.e. to treat a condition ameliorated by the delivery of therapeutic or nutritional silicate. Preferably, the stabilised polymeric silicate composition when formulated for oral delivery is a liquid filled capsule. This may be to treat a condition in the GI tract or for the purpose of silicon supplementation. The former may involve iron binding to ameliorate iron's toxic effect in the colon. This and other embodiments of oral delivery may require enteric or specialist coating for delayed release.

In a further application, the stabilised polymeric silicate compositions may be administered to a subject intravenously by dilution into a drip, typically a glucose or saline or sucrose drip, with or without a buffer or agent to achieve a pH suitable for administration. In this aspect of the present invention, the determination of doses suitable for providing given levels of silicate in circulation can be determined by doctors using approaches well known in the art.

In an alternative application, the stabilised polymeric silicate compositions may be formulated for topical administration for example for application to the skin or surface of wounds.

Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Where the silicate-containing supplement needs to be maintained in a solid form, e.g. to control the delivery of a component of the material, it may be necessary to select components of the formulation accordingly, e.g. where a liquid formulation of the material is made. Preservatives, stabilisers, buffers, antioxidants and/or other additives may be included, as required, for example in embodiments of the present invention in which the polymeric silicate compositions are suitable for administration to a subject via a drip.

In therapeutic applications, stabilised polymeric silicate compositions of the present invention are preferably given to an individual in a "prophylactically effective amount" or a "therapeutically effective amount" (as the case may be, although prophylaxis may be considered therapy), this being sufficient to show benefit to the individual (e.g. bioavailability). The actual amount administered, and rate and time-course of administration, will depend on the nature and severity of what is being treated. Prescription of treatment, e.g. decisions on dosage etc. is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, Lippincott, Williams & Wilkins. A composition may be administered alone or in combination with other treatments, either simultaneously or sequentially, dependent upon the condition to be treated.

The compositions of the present invention may be used in therapeutic applications in which delivery of silicate is desirable, including a wide array of medical conditions that include, but are not limited to, osteoporosis, osteopenia, musculoskeletal and joint disorders, cancers of all types, skin conditions, vascular diseases, cardiovascular diseases, coronary heart diseases, inflammatory diseases, autoimmune diseases, Alzheimer's disease, cognitive impairment, infections of all types, wounds, ulcers, gastrointestinal disorders, liver disease, kidney disease, immune related disorders or hormone related disorders. Cosmetic aspects of the present invention include the cosmetic improvement of hair, skin or nails, e.g. to provide them with an improved appearance. The compositions of the present invention may also be used in veterinary therapeutic applications in which delivery of silicon is desirable, including, but not limited to, treatment of wounds, ulcers and cancers. The therapeutic uses of silicates are disclosed in WO 2009/052090, US Patent Publication No: 2009/0130230 and US Patent Publication No: 2013/0149396, incorporated by reference in their entirety, and in particular the compositions of the present invention may be used in the treatment of conditions disclosed in these references with the added advantage that the compositions of the present invention are stabilised.

In a further aspect, the polymeric silicate compositions of the present invention may be delivered orally not as bio-available silicon but, rather, to keep it in the distal gut lumen where absorption is low, and to utilise the strong binding affinity of polysilicic acid for certain cations, notably iron. Recent evidence shows that iron in the colon is permissive for the development of colonic cancers in susceptible individuals (13). Thus, in a further embodiment, the delivery of stabilised polymeric silicate compositions targeted to the colon, at concentrations that once in that environment favours only gradual dissolution or even condensation of the polysilicic acid will result in complexation/deactivation of luminal iron and, thereby, prevention or reduction of tumorogenesis in the local environment. This may be useful in the treatment or prevention of cancer in the colon.

During infection and chronic disease, such as cancer, the body induces an anaemic state, partly through the reduced mobilisation of iron and the reduced shuttling of iron between different cellular and extracellular compartments. The iron is locked up into ferritin. This is because loose iron can enhance infection and chronic disease states and so it needs to be sequestered. Indeed, one commonly proposed strategy in disease treatment is the sequestration of iron with chelators that lock it into an immobile state. The finding that polymeric silicate compositions of the present invention (e.g. SANS and uSANS) can mop up iron means that when appropriately formulated for administration to a subject, these may have a clinical role in sequestering iron and helping combat disease. This may be through the binding of iron in the gastrointestinal lumen thereby preventing iron's ingress to the body and/or toxicity to intestinal cells, such as in the colorectal region, or may be a systemic effect following parenteral administration in cellular and/or extracellular compartments.

Silicate nanoparticles that are transiently stable in vivo may have suitable roles for re-activation of the immune system to help treat infections and cancers, for example. Cancers may include but are not restricted to: melanoma, skin cancers, lung cancer, pancreatic cancer, colon rectal and other splanchnic cancers, gastric cancer, breast cancer, lymphomas, leukaemias, uterine cancers, prostate cancer, oesophageal cancer, bone cancers, bladder cancers, cervical cancer, endometrial cancer, brain cancer, eye cancers, ovarian cancer, testicular cancer, liver cancer, renal cancer, head and neck cancers and includes metastatic and primary cancers. Infection includes, but is not limited to: infection with viruses, retroviruses and bacteria such as Mycobacteria, Gram positive bacteria and Gram negative bacteria, as well as helminths, parasites and other infectious agents.

The transiently stable silicate nanoparticles may also act as a reservoir for the release of silicic acid that itself is effective in enhancing connective tissue health and may be useful in osteoporosis, fracture healing, joint diseases, skin diseases, blood vessel disorders, or for nutritional supplementation to ensure adequate supply of silicate.

As such, administration may be by topical application, oral administration or parenteral administration, the latter especially by intravenous administration.

Other medical uses of the compositions of the present invention include the treatment of hypertension, diabetes, bone diseases, cardiovascular diseases, neurodegenerative pathologies, cancer of all types not noted above, hyperacidity, osteoporosis, dental calculus, Alzheimer disease, Creutzfeld-Jacob disease as well as for wound healing.

Other medical uses of the compositions of the present invention include the treatment of skin affected by burn, wounding or action of pathogens or of caustic chemicals, including the treatment of sun burn, or any skin disease including psoriasis, eczema and dermatitis of other sorts.

Polyalkylene glycols such as PEG are especially well suited for topical delivery of silicate as it forms an ointment and is available in a range of different molecular weights, allowing the tailoring of viscosity and other physical parameters that may desirable in the final ointment.

It will be obvious to those in the art that topical application delivery may be achieved using non- or only partially PEG based ointments. In this case, upon initial stabilisation with PEG as described herein, the silicates are incorporated in a non-PEG based ointment, e.g. a PEG stabilised nanosilicate composition incorporated in a further, different vehicle such as hydroxyethyl cellulose.

An effective amount of one or more stabilised polymeric silicate compositions herein may be formulated for topical application, e.g. to the skin, teeth, nails or hair. These compositions can be in the form of creams, lotions, gels, suspensions, dispersions, microemulsions, nanodispersions, microspheres, hydro gels, emulsions (oil-in-water and water-in-oil, as well as multiple emulsions) and multilaminar gels and the like, (see, for example, The Chemistry and Manufacture of Cosmetics, Schlossman et al., 1998), and may be formulated as aqueous or silicone compositions or may be formulated as emulsions of one or more oil phases in an aqueous continuous phase (or an aqueous phase in an oil phase). The type of carrier utilized in the present invention depends on the properties of the topical composition. The carrier can be solid, semi-solid or liquid. Suitable carriers are liquid or semi-solid, such as creams, lotions, gels, sticks, ointments, pastes, sprays and mousses. Specifically, the carrier is in the form of a cream, an ointment, a lotion or a gel, more specifically one which has a sufficient thickness or yield point to prevent the particles from sedimenting. The carrier can itself be inert or it can possess benefits of its own. The carrier should also be physically and chemically compatible with the stabilised polymeric silicate compositions or other ingredients formulated in the carrier. Examples of carriers include water, hydroxyethyl cellulose, propylene glycol, butylene glycol and polyethylene glycol, or a combination thereof.

Materials and Methods

Preparation of Small Amorphous Nano-Silicates (SANS)

A 25±5 mM solution of silicate was prepared from a concentrated stock of sodium silicate. Next, an HCl solution was used to adjust pH to 6.8±0.2. The pH drop resulted in the formation of amorphous colloidal silicates. The solution was left to equilibrate for 16-24 hours during which it increased to pH 7.1±0.2. The process leading to the formation of the stabilised polymeric silicate compositions of the present invention is shown schematically in FIG. 1.

Methodology

The aliquots were diluted to ca. 1 mM in 10 mM HEPES buffer and pH adjusted, if needed, to pH 6.7-7, 25 h after initial SANS stock preparation. A molybdic acid assay was used to determine concentration of soluble silicate over time.

Molybdic Acid Assay

100 µL of the test solution or standard (prepared from Sigma Aldrich Si ICP standard, 1000 mg/L) and 200 molybdic acid colouring solution (0.6105 g $NH_4Mo_7$ $4H_2O$, 15 mL 0.5 N $H_2SO_4$, 85 mL $H_2O$) were transferred to a 96 well plate and mixed for 10 min. After the incubation, the absorbance (405 nm) was measured the concentration of soluble silicic acid was determined using the standard curve.

PEG Stabilised Ultra Small Amorphous Nano-Silicates (uSANS)

A suspension of nanoparticulate silicates (0.5M Si) was prepared by first diluting a concentrated solution of sodium silicate (resulting pH is greater than 10.5) and then dropping the pH to approximately 1.0 in less than 5 sec by a bolus addition of concentrated HCl. The pH was then raised to 3.0 and 1M PEG 200 added. This suspension was then diluted to 1 mM Si (24 h later) for the dissolution assay.

Non-Stabilised Ultra Small Amorphous Nano-Silicates (uSANS)

The same process was used as for the PEG-stabilised material (0.5 mM; pH 3), but without addition of PEG.

Change in Particle Size Upon Raising a Non-Stabilised Suspension of Ultra Small Amorphous Nano-Silicates (uSANS; 0.5 M) to pH 7.0

A non-stabilised suspension of uSANS (0.5M Si) was prepared by first diluting a concentrated solution of sodium silicate (resulting pH is greater than 10.5) and then dropping the pH to approximately 1.0 in less than 5 sec by a bolus addition of concentrated HCl, and then raising it to pH 3.5. The suspension was subsequently diluted to 40 mM and the pH raised to 7.0 to induce controlled particle growth.

Change in Particle Size Upon Raising a Non-Stabilised Suspension of Ultra Small Amorphous Nano-Silicates (uSANS) (0.5 M) to pH 4.0

Process:

A non-stabilised suspension of uSANS (0.5M Si) was prepared by first diluting a concentrated solution of sodium silicate (resulting pH is greater than 10.5) and then dropping the pH to approximately 1.0 in less than 5 sec by a bolus addition of concentrated HCl. The pH was then raised to 4.0 to induce controlled particle growth.

Transient Particle Size Stability at pH 4.0 of a Suspension of uSANS (0.5M) Stabilised with PEG A non-stabilised suspension of nanoparticulate silicates (0.5M Si) was prepared by first diluting a concentrated solution of sodium silicate (resulting pH is greater than 10.5) and then dropping the pH to approximately 1.0 in less than 5 sec by a bolus addition of concentrated HCl. The pH was then raised to 4.0 and 1M PEG added.

Particle Size Stability of Sucrose Stabilised Ultra-Small Amorphous Nano-Silicates (uSANS) at Physiological pH A sucrose-stabilised suspension of uSANS (0.5M Si) was produced by diluting a concentrated solution of sodium silicate (resulting pH is greater than 10.5) and adding sucrose (such that the final composition contains 1.5M sucrose). Next the pH was dropped to approximately 1.0 in less than 5 sec by a bolus addition of concentrated HCl. This was followed by sodium hydroxide addition to obtain pH 3.5. Next, this suspension was diluted down to 40 mM Si and the pH adjusted to 7 to simulate intravenous administration.

Size of Small Amorphous Nano-Silicates (SANS) Particles Before and after Freezing Fresh SANS suspension (30 mM, preparation as in FIG. 3) was kept at −20° C. for 16 hours and thawed 1-3 hours prior to incorporation into PEG cream.

Silicon Release from Disperse and Agglomerated Small Amorphous Nano-Silicates (SANS) Particles (Both at 5 mM) in a PEG Cream Release Assay:

Si-containing PEG creams (10 g) were transferred to and allowed to settle at the bottom of a Falcon tube for at least 12 hours. Next, 10 ml of a 50 mM bicarbonate buffer (pH 7) was added on top of the cream layer and the release of silicon determined overtime by ICP-OES. The assay was run at room temperature ~20° C. Agglomerated materials were produced by freezing and thawing as described above.

Incorporation into a PEG Cream

PEG 3350 (5.25 g) was melted. A SANS suspension (2.3 g of 30 mM suspension) is mixed with PEG 400 (6.15 g) at 65-70° C. and added to the PEG melt. The resulting mixture was homogenised and allowed to cool to room temperature.

Figure 12:
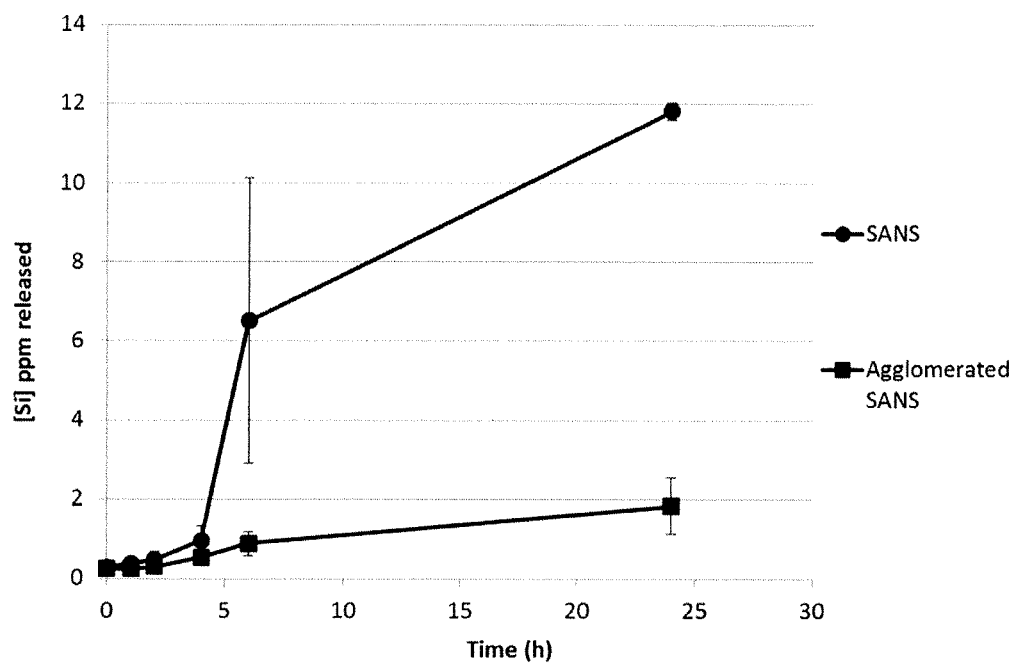
FIG. 12. Silicon release from disperse and agglomerated small amorphous nano-silicates (SANS) particles (both at 5 mM) in a PEG ointment.

Silicon Release from SANS Particles (5 mM Si) and uSANS (40 and 60 mM Si) in a PEG Cream Methodology:

Same as described in FIG. 12.

Incorporation of uSANS into a PEG Cream

Method 1:

PEG 3350 (5.25 g) was melted and sodium hydroxide was added to ensure the pH of the cream, once formed, was above pH 6. PEG 200-stabilized silicate nanoparticles (2.3 g of 0.5M suspension) were mixed with PEG 400 (6.15 g) at 65-70° C. and added to the PEG melt. The resulting mixture was homogenised and allowed to cool to room temperature.

Method 2:

PEG 3350 (5.25 g) was melted and sodium hydroxide was added to ensure the pH of the cream, once formed, was above pH 6. PEG 200-stabilized silicate nanoparticles (2.3 g of 0.5M suspension) were mixed with PEG 400 (6.15 g) at room temperature and added to the PEG melt. The resulting mixture was homogenised and allowed to cool to room temperature.

Silicon Release from PEG 200-Stabilised Polymeric Silicate in a PEG Ointment

Stabilised silicate at pH 3 in which adjustment to pH 7 was carried out at different stages in the formation of the PEG cream.

Methodology:

The preparation of PEG ointments comprises the incorporation of PEG200-stabilised suspension (0.5 M Si; pH 3.0) into PEG cream, which further stabilised the materials. The cream was formed by first mixing the suspension PEG 400, followed by heating to 60-70° C. and then adding PEG 3350. The pH neutralisation was carried out adding NaOH after 1) PEG 200 stabilisation (before PEG 400), or 2) after addition of PEG 400, or 3) with the addition of PEG3350.

Figure 3:
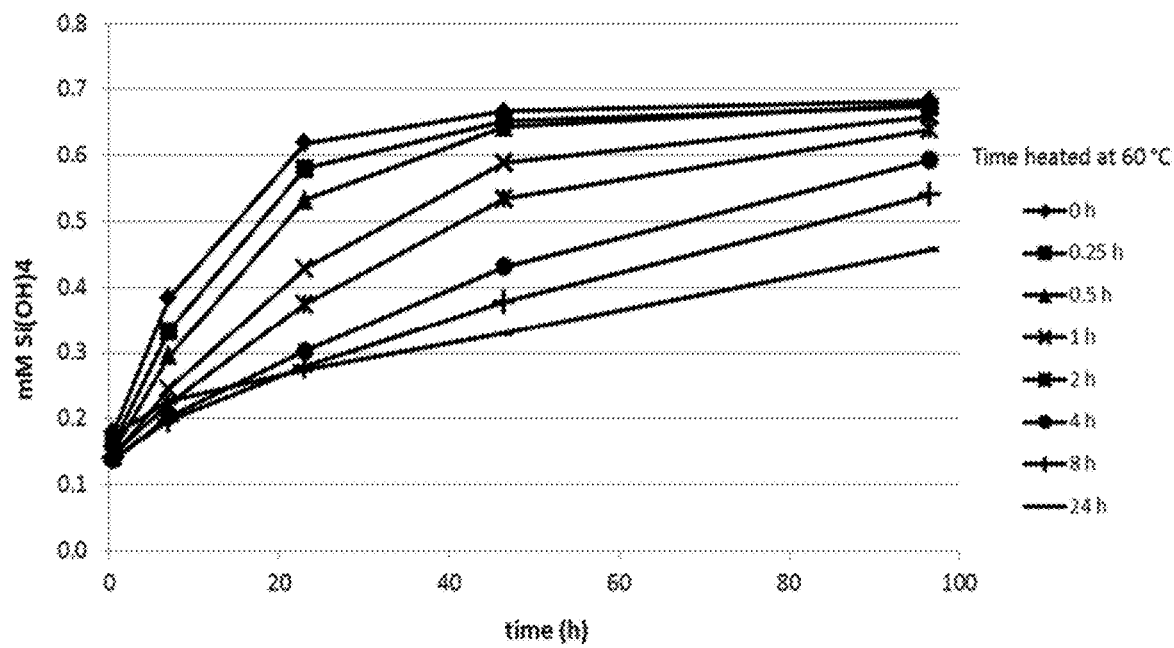
FIG. 3. Dissolution rates of small amorphous nano-silicates (SANS) after heating at 60° C. for various periods. Note that heating did not lead to changes in particle size (not shown).
Figure 4:
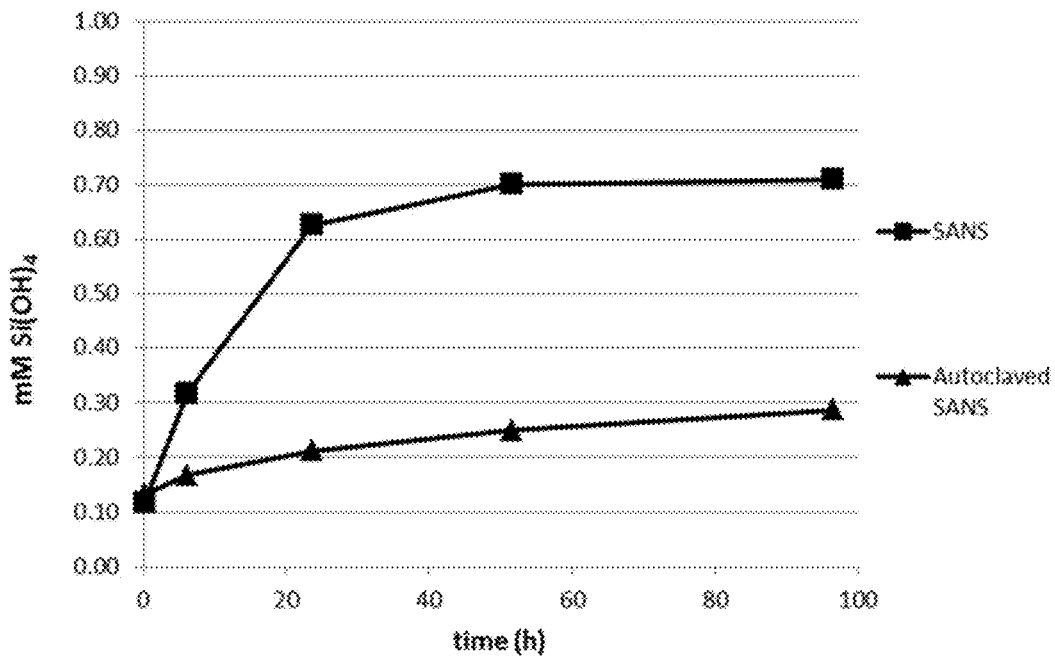
FIG. 4. Dissolution rates for small amorphous nano-silicates (SANS) before and after autoclaving (121° C. for 15 min).
Figure 5A:
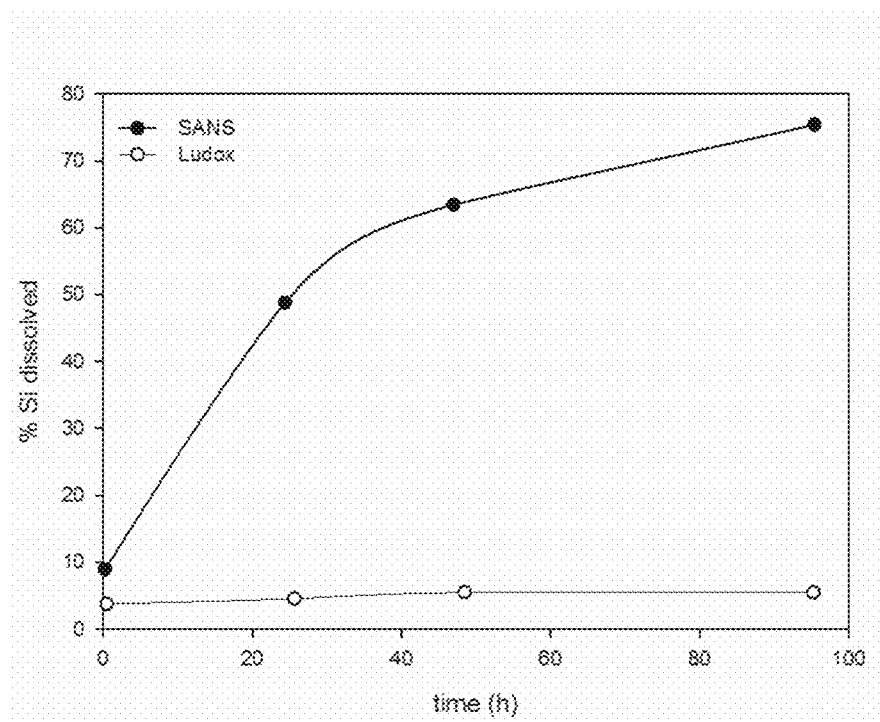
FIG. 5A-5B.
Figure 5B:
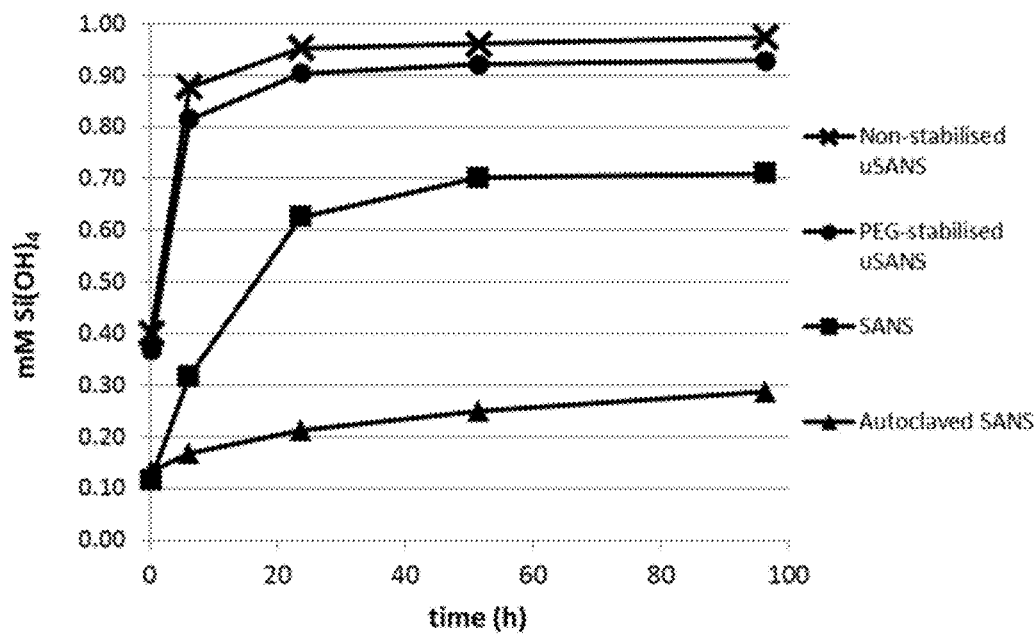
Figure 19:
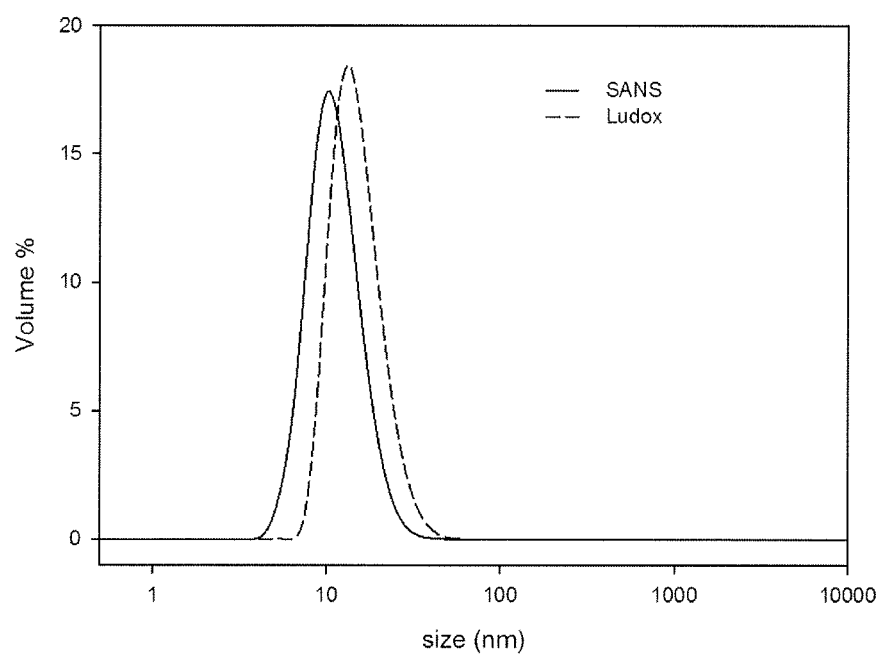
FIG. 19. Particle size of small amorphous nano-silicates and Ludox SM30® in water. SANS particle size was increased to approach the particle size of Ludox SM30® so dissolution can be compared independent of size. Size was increased by adding concentrated saline (1-2 mL, 1.54 M) to the nanosilica dispersion immediately after pH adjusting. This was done in so that the particle size of the Ludox SM30® was broadly similar to that of the SANS so that dissolution was not a function of particle size. The dispersion was incubated for ca. 24 h at room temperature prior to use.

Experiments to Produce and Test Features of the Stabilised Polymeric Silicate Compositions of the Present Invention Amorphous Poorly Condensed Materials Amorphous nanosilicates can exhibit different levels of condensation, which are not easily distinguished by standard techniques, such as XRD. The present inventors observed that exposure to even moderate temperatures (e.g. 60° C.) can lead, over time, to an increase in condensation that results in lower dissolution rates (FIG. 3). This unwanted change is particularly pronounced at higher temperatures, such as those employed in drying or sterilisation processes, where even short exposures result in a dramatic reduction in lability (FIG. 4). In contrast, the synthetic methods described herein produce stable nanoparticles that are labile, i.e. non-persistent in vivo (FIG. 5). For reference, Ludox SM30® is an example of a condensed silicate nanoparticle. FIG. 19 shows that while Ludox SM30® and the nanosilicates of the present invention have similar particle sizes, that their respective different rates of dissolution mean that dissolution rates are not size dependent.

Preparation of Small Amorphous Nano-Silicates (SANS)

A 30±3 mM solution of silicate was prepared from a concentrated stock of sodium silicate. Next, an HCl solution was used to adjust pH to 6.8±0.2. The pH drop resulted in the formation of amorphous polymeric silicates. The solution was left to equilibrate for 16-24 hours during which it increased to pH 7.1±0.2.

Methodology:

Upon preparation, a SANS suspension was prepared and immediately heated to 60° C. At specific time points, aliquots were collected and allowed to cool to room temperature. The aliquots were diluted to ca. 1 mM in 10 mM HEPES buffer and adjusted to pH 6.7-7, 25 h after initial SANS stock preparation. A molybdic acid assay was used to determine concentration of soluble silicate over time.

Molybdic Acid Assay:

100 µL of the test solution or standard (prepared from Sigma Aldrich Si ICP standard, 1000 mg/L) and 200 µL molybdic acid colouring solution (0.6105 g $NH_4Mo_7 \cdot 4H_2O$, 15 mL 0.5 N $H_2SO_4$, 85 mL $H_2O$) were transferred to a 96 well plate and mixed for 10 min. After the incubation, the absorbance (405 nm) was measured the concentration of soluble silicic acid was determined using the standard curve.

PEG Stabilised Ultra Small Amorphous Nano-Silicates (uSANS)

A suspension of nanoparticulate silicates (0.5M Si) was prepared by first diluting a concentrated solution of sodium silicate (resulting pH is greater than 10.5) and then dropping the pH to approximately 1.0 in less than 5 sec by a bolus addition of concentrated HCl. The pH was then raised to 3.0 and 1M PEG added. This suspension was then diluted to 1 mM Si (24 h later) for the dissolution assay.

Non Stabilised Ultra-Small Amorphous Nano-Silicates (uSANS)

The same process was employed as for the PEG-stabilised material (0.5 mM; pH 3), but without addition of PEG.

Size Tailorability

Figure 6:
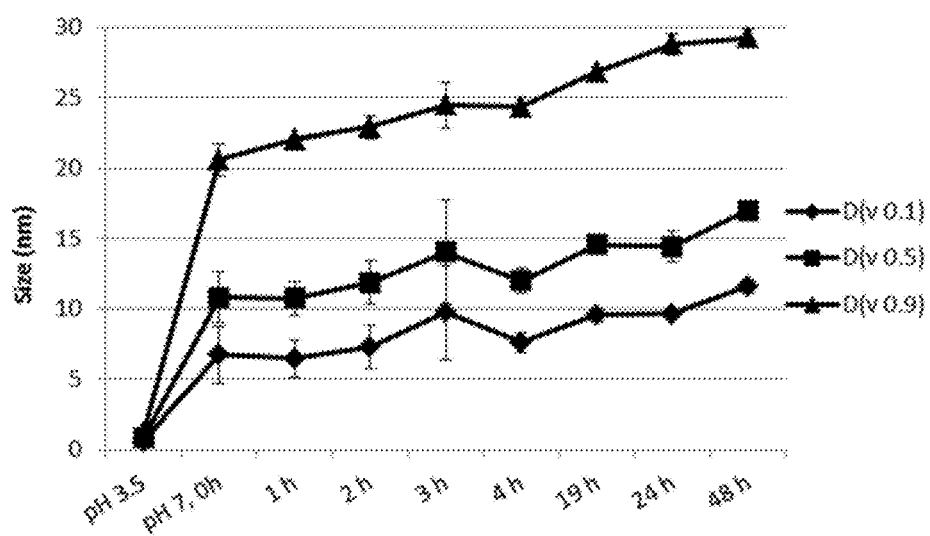
FIG. 6. Change in particle size upon raising a non-stabilised suspension of ultra small amorphous nano-silicates (40 mM) to pH 7.0.
Figure 7:
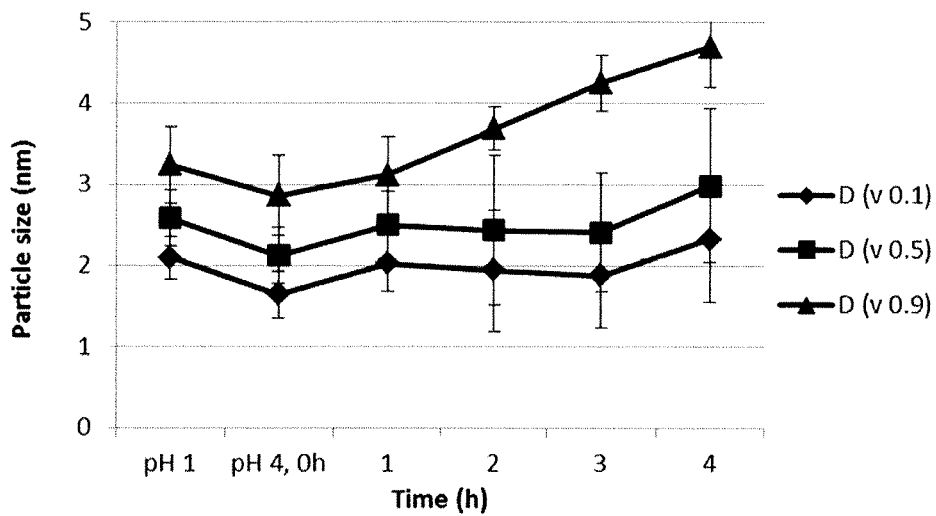
FIG. 7. Change in particle size upon raising the pH of a non-stabilised suspension of ultra small amorphous nano-silicates (0.5 M) to pH 4.0.
Figure 8:
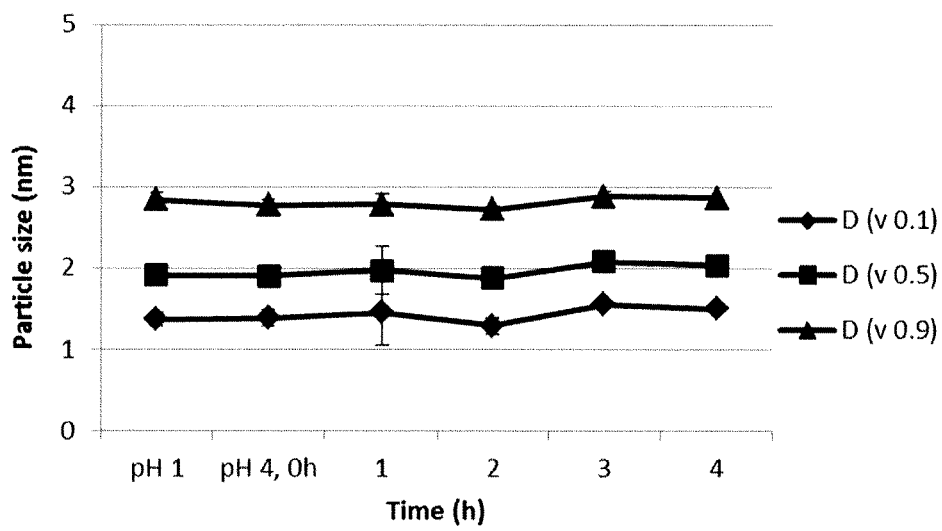
FIG. 8. Transient particle size stability at pH 4.0 of a suspension of ultra small amorphous nano-silicates (uSANS) (0.5M) stabilised with Sucrose (1.5).

Using the process described herein, upon dropping the pH, small particles (<5 nm; typically <3.5 nm) are formed. However, larger particle sizes can be achieved by raising the pH. FIG. 6 shows particle size growth upon raising the pH of a suspension of nanoparticles. Usefully, the rate of growth can be determined by selecting the appropriate pH and concentrations. FIG. 7 shows how a slower growth rate can be achieved by only raising the pH to 4. As stated above, size growth can be arrested by adding a stabiliser (e.g. PEG, FIG. 8) or diluting the suspension.

Transient Size Stability

Figure 9A:
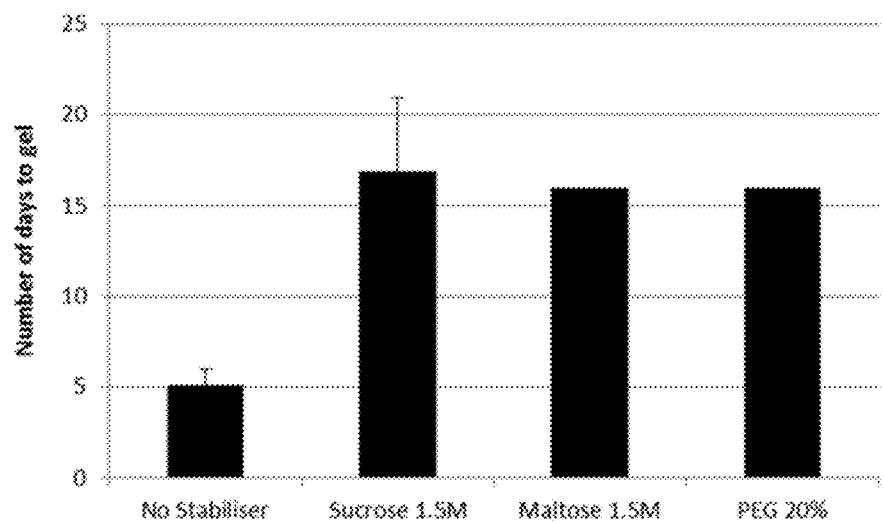
FIG. 9A-9B. Stability of ultra small amorphous nano-silicates suspensions (1.4% Si; i.e. 0.5 M). Nanoparticulate silicates were stabilised by various compounds at pH 3.5 (FIG. 9A). The effect of pH is also shown (FIG. 9B). The number of days required to form a gel was used as a proxy for stability. The results shown at pH 3.5 include a comparison of sucrose stabilised and non-stabilised materials.
Figure 9B:
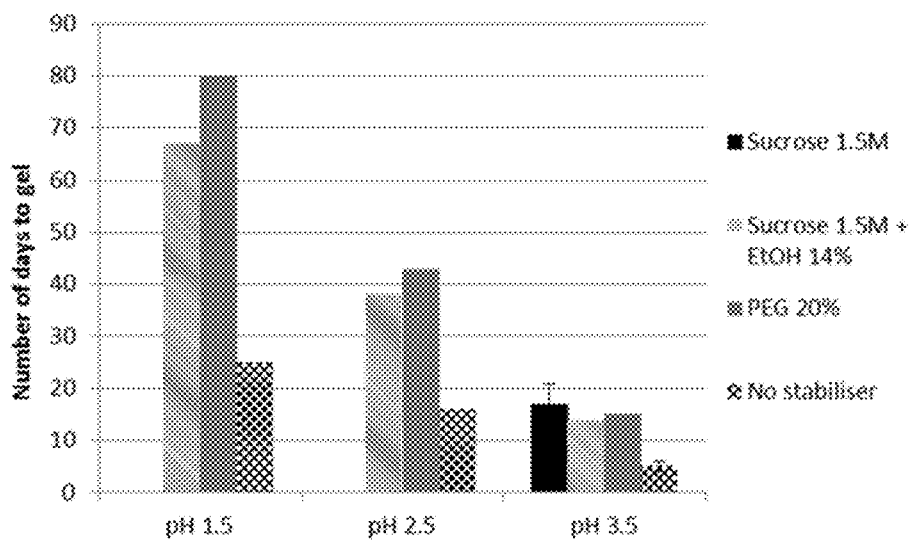

Growth retardants increase meta-stability (FIG. 9A) in a pH dependent fashion (FIG. 9B). This increase in stability enables the processing and formulation of concentrated amorphous silicates (e.g. incorporation in gels or creams).

Size Stability Under Physiological Conditions

Figure 10:
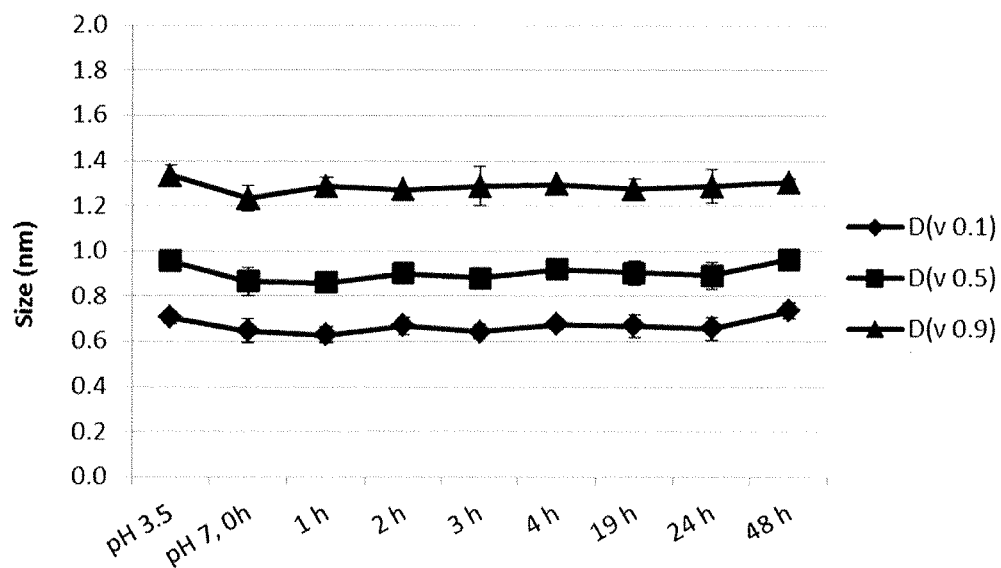
FIG. 10. Particle size stability of sucrose-stabilised ultra-small amorphous nano-silicates (uSANS) at physiological pH.

The enhanced dispersibility and stability of the silicates described herein allow the administration of high concentrations of nanoparticles at physiological pHs without the risk of aggregation. This enables a range of applications relying on parenterals, such as intravenous (i.v.), or oral delivery, and is illustrated by sucrose stabilised silicate NPs, which remain disperse and small once exposed to physiological pHs (FIG. 10).

Incorporation into a Solid or Semi-Solid Matrix

Figure 11:
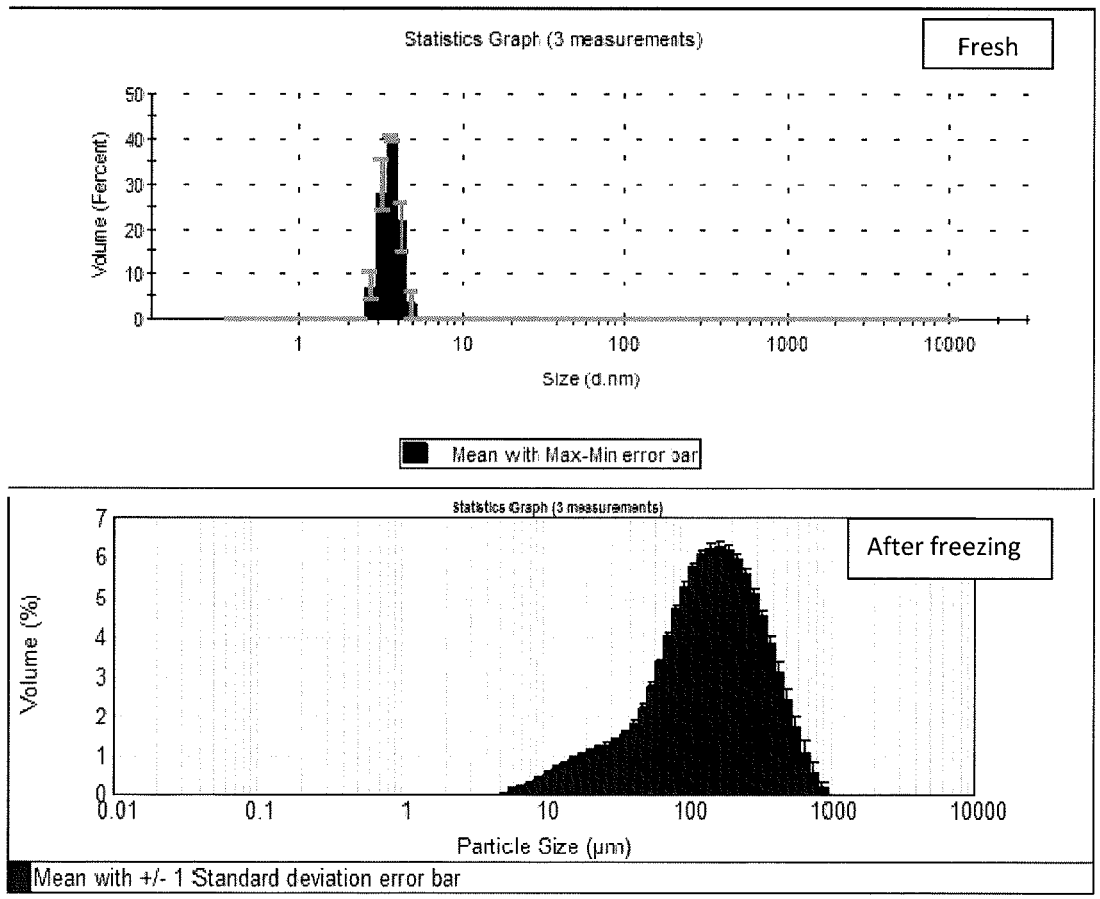
FIG. 11. Size of small amorphous nano-silicates (SANS) particles before and after freezing.

Effective release of silicon from silicate particles in a cream requires that particles remain non-agglomerated. To illustrate this, the agglomeration of non-stabilised amorphous silicates was induced by freezing (FIG. 11) prior to incorporation in a PEG cream. As a result, the release of silicon to a simulated physiological fluid in contact with the cream was considerably lower for the agglomerated particles (FIG. 12).

Figure 13:
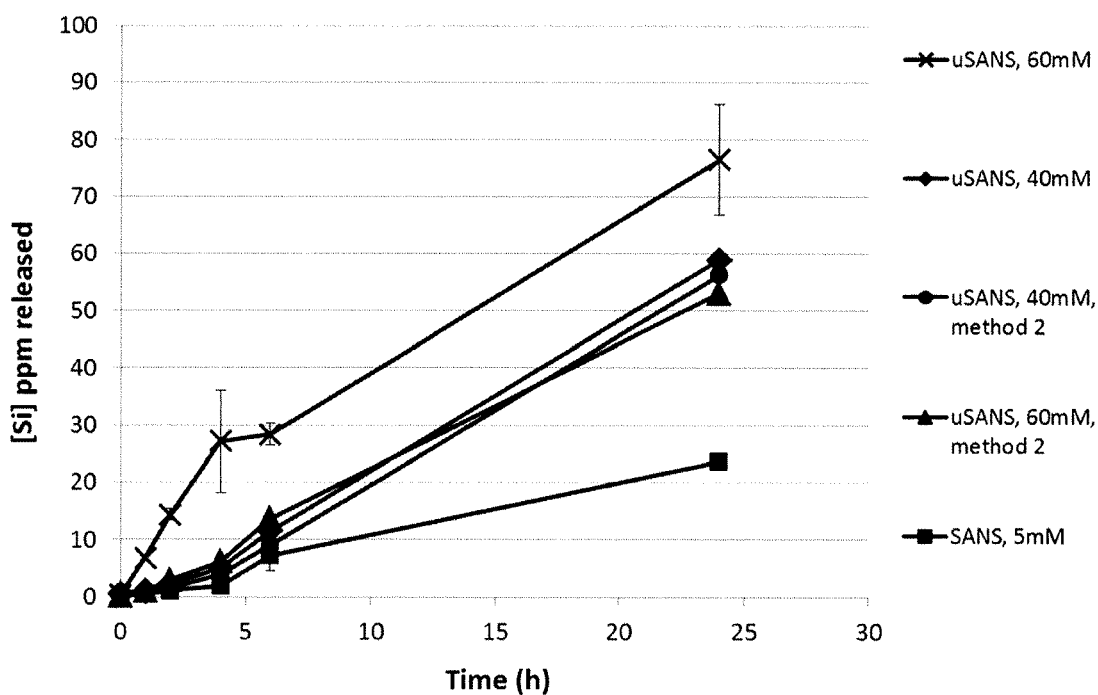
FIG. 13. Silicon release from small amorphous nano-silicates particles (SANS; 5 mM Si) and ultra small amorphous nano-silicates (uSANS 40 and 60 mM Si) in a PEG ointment as per FIG. 12.

As stated above, to preserve silicates in a poorly condensed form these should be kept as aqueous suspensions. However, the incorporation of aqueous suspensions into creams results in a considerable dilution factor (typically 5-7 fold) of the silicate active. Also, given that suspensions of unstabilised amorphous silicates at physiological pH (pH 6-8) are not stable above 40 mM, their final concentration in the cream is limited to ~8 mM. However, using the stabilisation strategies described herein, high concentrations of amorphous poorly condensed nanoparticles can be incorporated into PEG creams and result in greater release of the active agent (FIG. 13). The inventors have also discovered that to prevent agglomeration, the pH adjustment of the material is advantageously carried out once particles are fully stabilized by all PEG components (FIG. 14).

TEM Analysis

Figure 14:
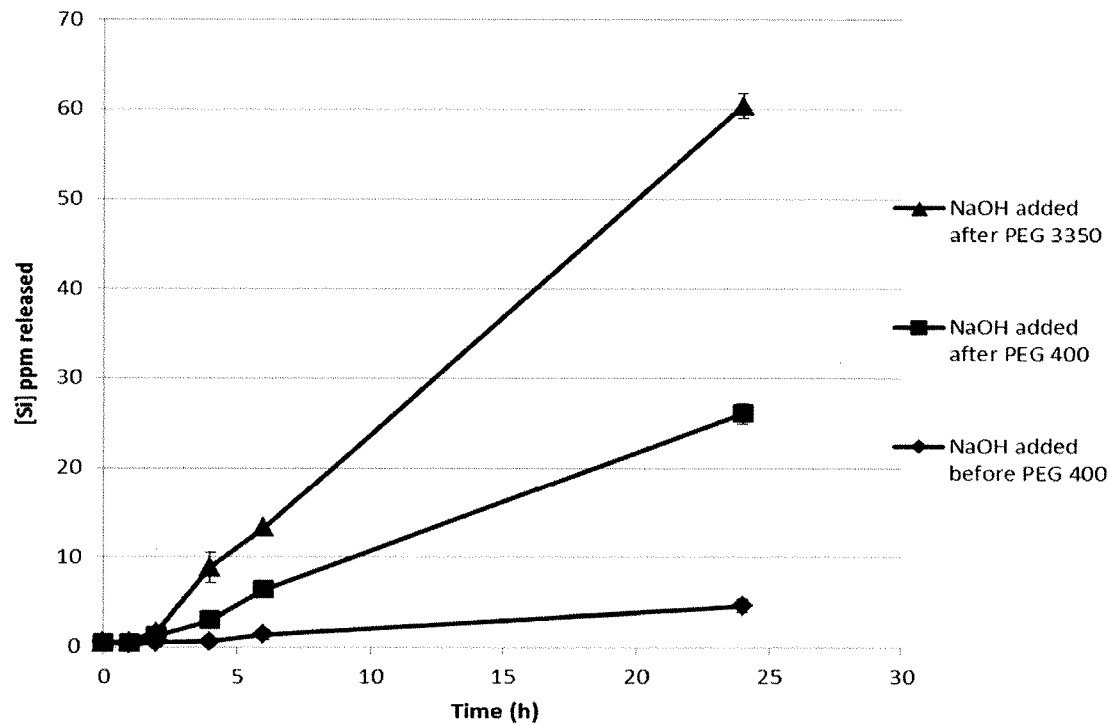
FIG. 14. Silicon release from PEG 200-stabilised silicate at pH 3 in which adjustment to pH 7 was carried out at different stages in the formation of the PEG ointment. Note that the silicate material was first stabilised with PEG 200 and then PEG 400 and PEG 3350 were added to form the ointment.

TEM analysis was carried out using an ointment made using the synthesis in FIG. 14 in which NaOH was added after PEG 3350. A small amounts ointment was suspended in ethanol. After sonication, a drop of this suspension was placed on a grid, and after drying, was examined in a FEI Tecnai F20 field emission gun (FEG) transmission electron microscope (TEM). The Tecnai F20 FEG-TEM was operated at 200 kV and is equipped with a Gatan Orius SC600A CCD camera and an Oxford Instruments X-Max energy dispersive X-ray (EDX) spectrometer. The final concentration of Si was 83 mmol/kg as determined using EDX spectroscopy which indicated the presence of silica as well as Cu. The TEM image showed the nanoparticles of stabilised polymeric silicates surrounded by a matrix of stabilising PEG 3350.

Iron Sequestration

Figure 15:
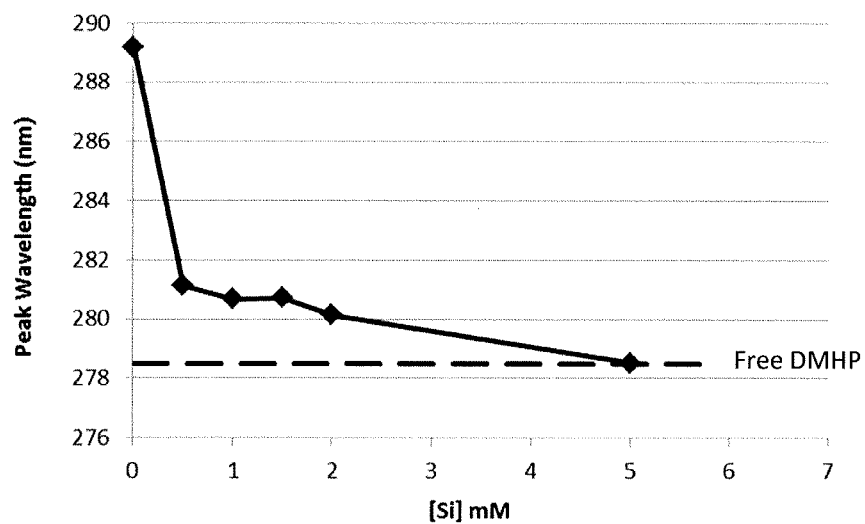
FIG. 15. Reduction in peak wavelength with increase of [Si], showing that DMHP was released from Fe-DMHP complex in the presence of stabilised silicate materials. Dashed line indicates the peak obtained for free DMHP in the absence of Fe.
Figure 16:
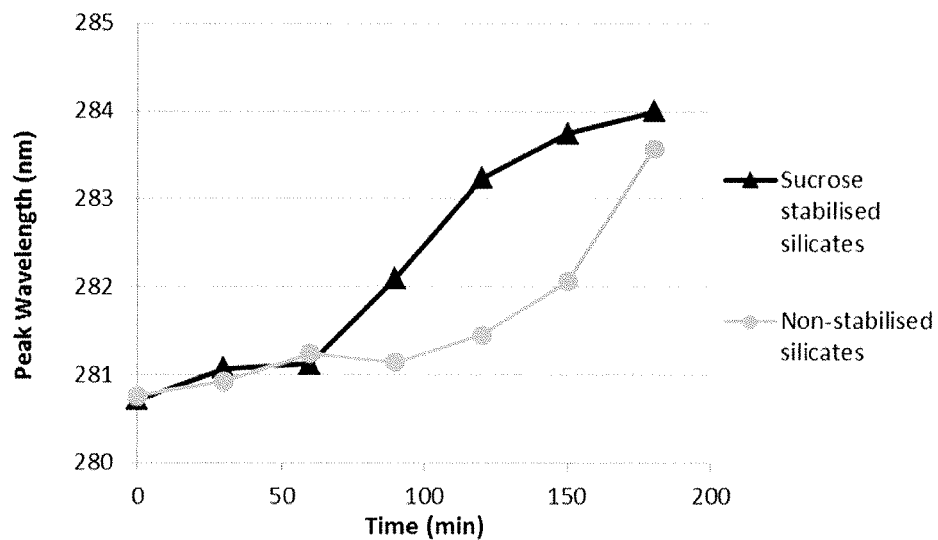
FIG. 16. Peak wavelength shift over time following iron sequestration by stabilised and non-stabilised ultra small amorphous nano-silicates (both at 1.5 mM).

Silicate stabilised materials remove Fe from Fe-DMHP complex; at 5 mM Si (Ratio 1:625 Fe:Si), all DMHP was unbound from the Fe complex (FIG. 15). However, over time DMHP seemed to complex iron again as seen by a shift towards the Fe-DMHP wavelength (289.2 nm) in both stabilised and non-stabilised silicates (FIG. 16).

Antimicrobial Action of Copper Loaded Si NPs

Figure 17:
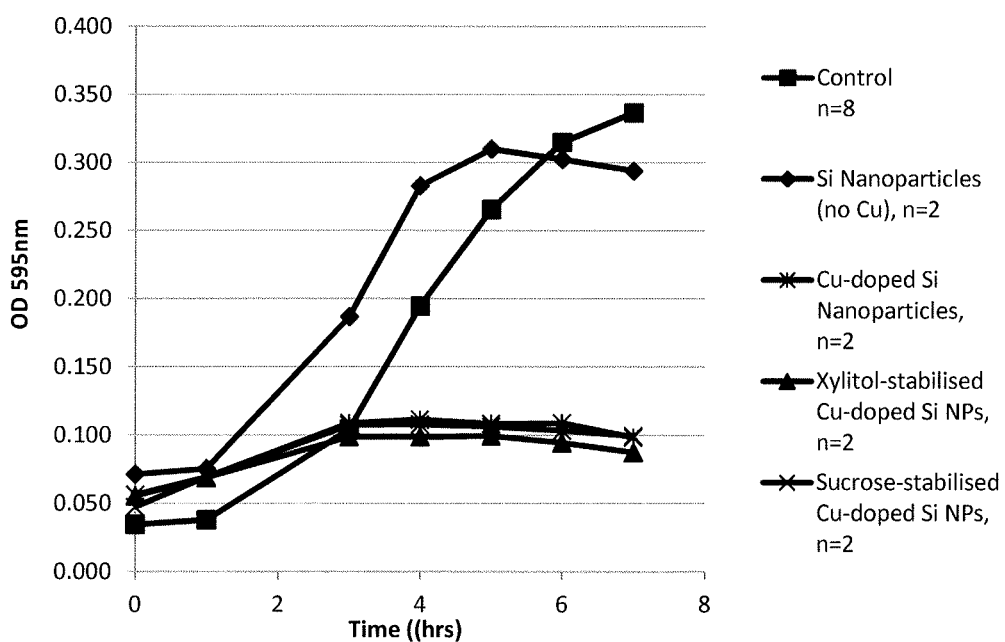
FIG. 17: *E. coli* growth curves over time in the presence of different Si ultra small amorphous nano-silicates.
Figure 18:
FIG. 18. Experiment to show the effect of drying lactose containing silicates at 200'C as described in U.S. Pat. No. 5,807,951. Large black visible agglomerates were formed after 4 hours of drying, dramatically altering the material produced.

Copper loaded silicate polymers showed antimicrobial activity, but Growth retardants did not impact negatively in the bacterial activity of copper. There was not a remarkable difference between stabilised and non-stabilised materials (FIG. 17). In practice, stabilisation would allow greater copper-loaded silicate concentrations and no impact of the stabiliser on efficacy.

Stabilised Polymeric Silicate Compositions for GI Administration

Compositions of the present invention may be tested to determine their behaviour in the gastrointestinal tract. After exposure to simulated digestion, the compositions undergo a rapid change such that some silicic acid is released, that would be absorbed and utilised by the body, whilst the remaining silicate forms larger particles that would be safely excreted in the faeces.

Persistent nanoparticles and the concurrent risk of toxicity are therefore avoided.

Stabilised Polymeric Silicate Compositions for i.v. Administration

The gradual dilution of stabilised polymeric silicate compositions stabilised using sucrose at pH 4.0 nanoparticles was tested in a tubing containing saline at pH 7.4 and in equilibrium with a larger body of saline, thereby mimicking intravenous injection. Silicic acid is very rapidly formed enabling safe parenteral delivery. Particle formation is not observed under these conditions. but even if it were to happen, the reticuloendothelium system would scavenge them effectively. Exposure to potentially toxic nanoparticulate silicate is minimum.

Stabilised Polymeric Silicate Compositions Formulated in a Solid or Semi-Solid Matrix for Topical Application Stabilised polymeric silicate compositions, optionally doped with copper, of the present invention were incorporated in a hydroxy ethyl cellulose gel (2% w/w) and for covering wounds. Optionally metal ions such as $Cu^{2+}$ or $Ag^+$ may be included in the cream for increasing its antibacterial properties.

Lactose Treatment by Heating and Particle Size Stability According to U.S. Pat. No. 5,807,951

Figure 2A:
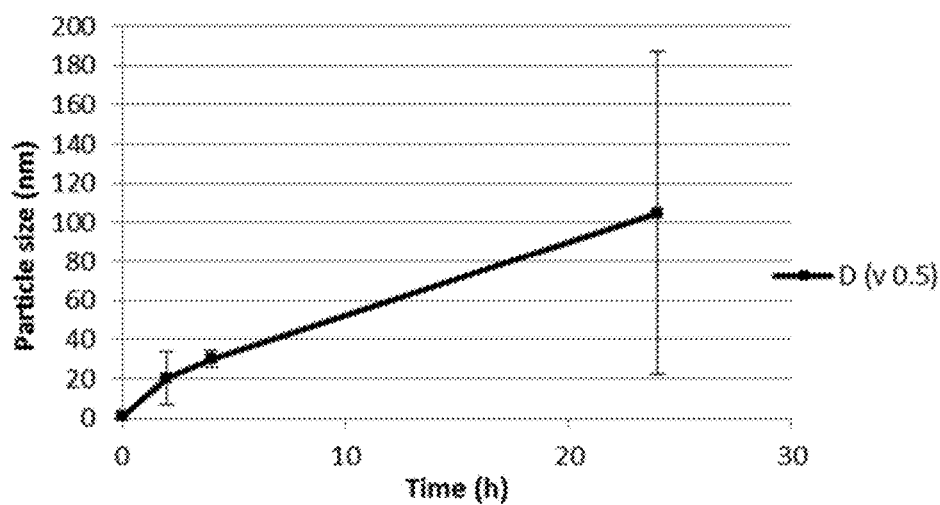
FIG. 2A-2B. Particle size of lactose containing silicates prior to drying.
Figure 2B:
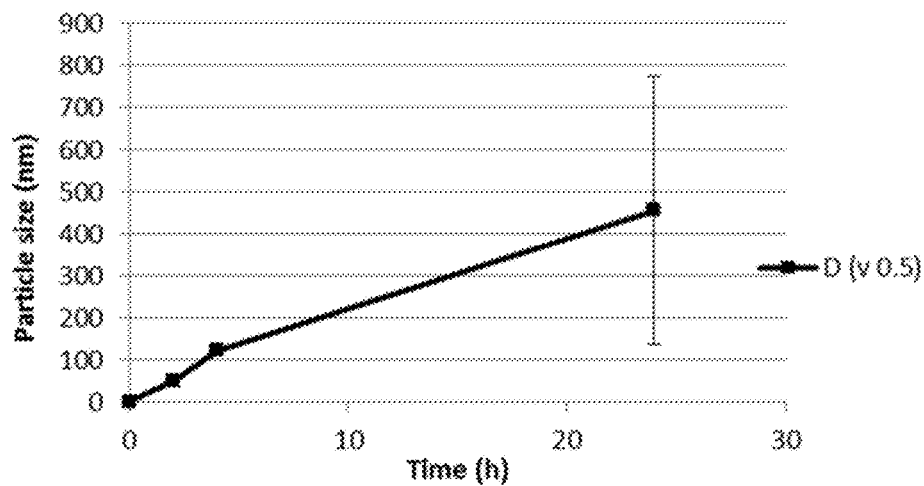

0.91 g of sodium metasilicate pentahydrate was dissolved in 10 ml of UHP water. 9.6 g of lactose was dissolved in 30 ml of UHP water at 50° C. for 30 minutes. Both solutions were mixed and adjusted to pH 8 with 0.5M HCl. The final material containing approximately 70 mM Si was analysed for particle size by DLS (A). An aliquot was collected, diluted to 40 mM and adjusted to pH 7 to mimic physiological conditions. This diluted suspension was also characterised for particle size (B). The same protocol as in FIG. 2 and the final suspension, approximately 70 mM Si at pH 8, was dried at 200° C.

Control of Dissolution Using Metal Ions

Figure 20:
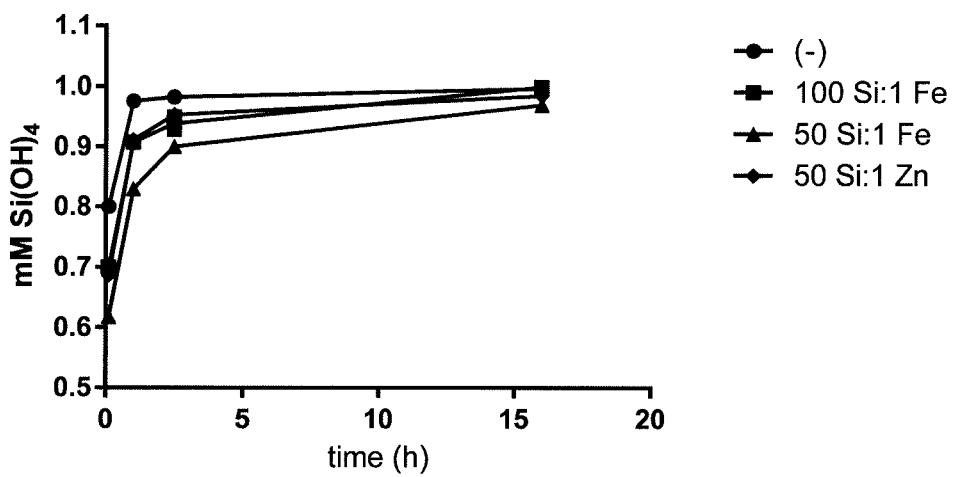
FIG. 20. Dissolution rates as determined by the molybdate assay for uSANS dispersions (500 mM Si, pH 1.5) before and after spiking with soluble metal ions.
Figure 21:
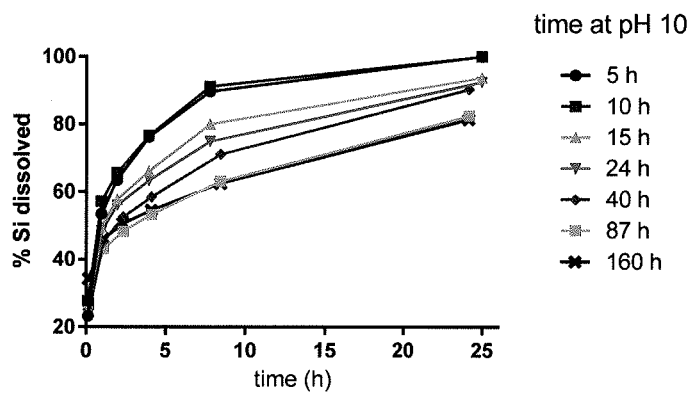
FIG. 21. Dissolution rates as determined by the molybdate assay for a uSANS dispersion (500 mM Si, pH 1.5) after various incubation periods at pH 10.

A uSANS dispersion (500 mM Si, pH 1.5) was spiked with soluble metal ions and incubated at room temperature for 1 h. FIG. 20 shows that low levels of metals inhibit the dissolution of uSANS as determined by the molybdate assay.

REFERENCES

All documents mentioned in this specification are incorporated herein by reference in their entirety.

Jugdaohsingh et al., Is there a biochemical role for silicon?, in Metal Ions in Biology and Medicine, Volume 10, pages 45-55, 2008, John Libbey Eurotext: Montrouge.

WO 2009/052090.

US Patent Publication No: 2009/0130230.

US Patent Publication No: 2013/0149396.

U.S. Pat. No. 5,807,951 (Nippon Zoki Pharmaceutical Co., Ltd.)

US Patent Publication No: 2011/0229577 (Kerek).

Kim et al. (Macromolecules, 45: 4225-4237, 2012).

Gao et al (Colloids and Surfaces A: Physicochem. Eng. Aspects

The invention claimed is:

1. A process for producing a stabilised polymeric silicate composition comprising polymeric silicic acid and nanosilicate particles having mean diameters of 20 nm or less, the process comprising the steps of:
    (a) providing an aqueous solution of a soluble silicate at a pH greater than or equal to 9.5;
    (b) reducing the pH of the silicate solution to cause polymerisation of the silicate to form polymeric silicic acid and nanosilicate particles, wherein the pH is lowered over a period of less than 60 seconds; and
    (c) simultaneously or sequentially with steps (a) and/or (b) adding to the silicate solution a stabilising agent that comprises a polyalkylene glycol and/or a sugar thereby producing a stabilised silicate composition in which the stabilising agent inhibits formation of condensed silicates;
    wherein the stabilised polymeric silicate composition is aquated and wherein the process does not involve drying the composition or heating it above 100° C.

2. The process of claim 1, wherein the stabilised polymeric silicate composition comprises at least 5% water.

3. The process of claim 1, wherein the process does not involve drying the composition or heating it above 70° C.

4. The process of claim 1, wherein the stabilised polymeric silicate composition is resorbable as determined in an in vitro dissolution assay in which at least 25%, and optionally at least 35%, of the composition dissolves in 24 hours in HEPES buffer.

5. The process of claim 4, wherein the in vitro dissolution assay is a molybdic acid assay for determining the soluble silicic acid fraction.

6. The process of claim 1, which comprises the further step after steps (b) and (c) of raising the pH of the composition to a final pH by adding a base, and optionally waiting for average particle size grow to the desired size and then optionally adding further stabiliser and/or dropping the pH.

7. The process of claim 1, wherein the base is sodium hydroxide or sodium carbonate.

8. The process of claim 1, further comprising formulating the stabilised polymeric silicate composition as a cream or ointment for topical administration to a subject.

9. The process of claim 8, wherein sodium hydroxide is added to adjust the pH of the composition prior to formulating the stabilised polymeric silicate composition as a cream or ointment by mixing with polyalkylene glycol.

10. The process of claim 8, wherein formulating the stabilised polymeric silicate composition as a cream or ointment comprises mixing it with a solid or semi-solid matrix.

11. The process of claim 10, wherein the solid or semi-solid matrix comprises one or more polyalkylene glycol polymers or one or more hydroxyethyl cellulose gels.

12. The process of claim 1, further comprising formulating the stabilised polymeric silicate composition so that it is formulated for oral administration or parenteral administration of silicic acid to a subject.

13. The process of claim 1, wherein in step (a) the aqueous alkaline silicate solution is a Group 1 or Group 2 metal silicate.

14. The process of claim 1, wherein in step (b) the pH is reduced to less than or equal to pH 4.0 by adding an acid.

15. The process of claim 1, wherein in step (c) the pH is reduced to less than or equal to pH 3.0.

16. The process of claim 1, wherein the concentration of the silicate solution is between 5 mM and 3.0 M.

17. The process of claim 1, wherein the concentration of the silicate solution is between 0.1 M and 1.5 M.

18. The process of claim 1, wherein the stabilised polymeric silicate composition is stable for 1 month or more, 2 months or more, 3 months or more, 6 months or more.

19. The process of claim 1, wherein the nanosilicate particles have a mean diameter of 10 nm or less.

20. The process of claim 1, wherein the nanosilicate particles have a mean diameter of 5 nm or less.

21. The process of claim 1, wherein the concentration of the silicate solution is more than 30 mM.

22. The process of claim 1, wherein in step (a) the pH of the alkaline silicate solution is above pH 11.5.

23. The process of claim 1, wherein two, three, four or five stabilising agents are added in step (c).

24. The process of claim 1, wherein the stabilising agent is sucrose or polyethylene glycol (PEG).

25. The process of claim 1, wherein the stabilising agent is not lactose or mannitol.

26. The process of claim 1, wherein in step (b) the pH of the composition is lowered to a pH less than or equal to pH 1.5.

27. The process of claim 1, further comprising adding one or more metal cations to the composition.

28. The process of claim 27, wherein the metal cation is $Cu^{2+}$, $Ag^+$, $Ca^{2+}$, $Mg^{2+}$, $Fe^{3+}$ and/or $Zn^{2+}$.

29. The process of claim 27, wherein the metal cation provides the composition with antibacterial properties.

30. The process of claim 28, wherein the metal cation is added to provide a Si to metal ratio of between 100:1 and 10:1.

31. The process of claim 13, wherein the Group 1 or Group 2 metal silicate is sodium silicate or potassium silicate.

32. The process of claim 30, wherein the metal cation is added to provide a Si to metal ratio of 20:1.

33. The process of claim 1, wherein in step (b) the pH is lowered over a period of less than 30 seconds.

34. The process of claim 1, wherein in step (b) the pH is lowered over a period of less than 10 seconds.

35. The process of claim 1, wherein in step (b) the pH is lowered over a period of less than 5 seconds.

\* \* \* \* \*